(12) United States Patent
Savage et al.

(10) Patent No.: US 12,097,212 B2
(45) Date of Patent: Sep. 24, 2024

(54) USE OF CATIONIC STEROIDAL ANTIMICROBIAL COMPOUNDS TO DEACTIVATE CORONAVIRUS

(71) Applicants: Paul B. Savage, Mapleton, UT (US); Michael C. Moore, Chandler, AZ (US)

(72) Inventors: Paul B. Savage, Mapleton, UT (US); Michael C. Moore, Chandler, AZ (US)

(73) Assignee: Brigham Young University, Provo, UT (US)

( * ) Notice: Subject to any disclaimer, the term of this patent is extended or adjusted under 35 U.S.C. 154(b) by 227 days.

(21) Appl. No.: 17/340,413

(22) Filed: Jun. 7, 2021

(65) Prior Publication Data

US 2021/0379091 A1     Dec. 9, 2021

Related U.S. Application Data

(60) Provisional application No. 63/036,413, filed on Jun. 8, 2020.

(51) Int. Cl.
| | | |
|---|---|---|
| *A61K 31/695* | (2006.01) | |
| *A61K 31/575* | (2006.01) | |
| *A61K 31/58* | (2006.01) | |
| *A61K 31/69* | (2006.01) | |

(52) U.S. Cl.
CPC .......... *A61K 31/695* (2013.01); *A61K 31/575* (2013.01); *A61K 31/58* (2013.01); *A61K 31/69* (2013.01)

(58) Field of Classification Search
None
See application file for complete search history.

(56) References Cited

U.S. PATENT DOCUMENTS

| | | | | |
|---|---|---|---|---|
| 6,767,904 B2 * | 7/2004 | Savage | ................ | C07J 41/0055 552/548 |
| 11,524,015 B2 * | 12/2022 | Savage | ................ | A61K 47/60 |
| 2007/0191322 A1 * | 8/2007 | Savage | ................ | A61K 31/568 435/5 |
| 2015/0110767 A1 * | 4/2015 | Savage | ................ | A61K 38/14 514/182 |

FOREIGN PATENT DOCUMENTS

| | | |
|---|---|---|
| WO | 2007/089903 A2 | 8/2007 |
| WO | 2008/048340 A2 | 4/2008 |
| WO | 2015/167962 A1 | 11/2015 |
| WO | 2019/113462 A1 | 6/2019 |
| WO | 2019/147831 A1 | 8/2019 |

OTHER PUBLICATIONS

McDonnell et al., "Antiseptics and Disinfectants: Activity, Action, and Resistance", 1999, Clinical Microbiology Reviews, vol. 12, No. 1, p. 147-179. (Year: 1999).*
Rumlová et al., "In vitro methods for testing antiviral drugs", 2018, Biotechnology Advances, vol. 36, Issue 3, pp. 557-576. (https://doi.org/10.1016/j.biotechadv.2017.12.016) (Year: 2018).*
Kathy Katella, "Our New COVID-19 Vocabulary—What Does It All Mean?", Apr. 7, 2020, https://www.yalemedicine.org/news/covid-19-glossary. (Year: 2020).*
Tarka et al., "Evaluating the Virucidal Activity of Disinfectants According to European Union Standards", 2021, Viruses, 13(4/534), pp. 1-9. (doi.org/10.3390/v13040534) (Year: 2021).*
Huang et al., "Evaluating the virucidal activity of four disinfectants against SARS-CoV-2", 2022, American Journal of Infection Control, 50, pp. 319-324. (https://doi.org/10.1016/j.ajic.2021.10.035) (Year: 2022).*
International Search Report and Written Opinion received for PCT Patent Application No. PCT/US21/036351, mailed on Sep. 15, 2021, 8 pages.
N8 Medical, LLC. "Health Canada Grants Emergency Use Authorization for N8 MedicalCeraShield(TM) Endotracheal Tubes in Mechanically VentilatedCOVID-19 Patients" Https://www.wfmz.com/news/pr_newswire/pr newswirehealth/health-canada-grants-emergency-use-authorizationfor-N8-medical-cerashield-tmendotracheal-tubes-in-mechanically/article2e6bBa78-2418-5aa8-b067-0c8fbc8c8d48.html. Apr. 2, 2020.
European Search Report received for EP Patent Application No. 21822593.6, mailed on May 22, 2024, 9 pages.
Howell et al., "Ceragenins: A class of Antiviral Compounds to Treat Orthopox Infections", Journal of Investigative Dermatology, vol. 129, No. 11, Jun. 11, 2009, pp. 2688-2675.

* cited by examiner

*Primary Examiner* — Kevin E Weddington
(74) *Attorney, Agent, or Firm* — Workman Nydegger

(57) ABSTRACT

The present disclosure describes compositions and methods for deactivating coronavirus. A method includes providing a deactivation composition including one or more CSA compounds and a carrier, administering the deactivation composition to a subject, and the deactivation composition deactivating coronavirus virions in the subject or coming into contact with the subject. The method can thereby prevent, decrease, or inhibit a coronavirus infection, such as COVID-19, of the subject.

20 Claims, 14 Drawing Sheets

CSA-37

CSA-41

CSA-42

CSA-43

CSA-44

CSA-45

CSA-47

CSA-49

CSA-50

CSA-51

CSA-1

CSA-2

CSA-3

CSA-4

CSA-5

CSA-6

CSA-7

CSA-8

CSA-10

CSA-11

CSA-118

CSA-119

CSA-120

CSA-121

CSA-121a

CSA-122

CSA-123

CSA-124

CSA-130

CSA-131

CSA-132

USE OF CATIONIC STEROIDAL ANTIMICROBIAL COMPOUNDS TO DEACTIVATE CORONAVIRUS

CROSS-REFERENCE TO RELATED APPLICATION

Figure 1A:
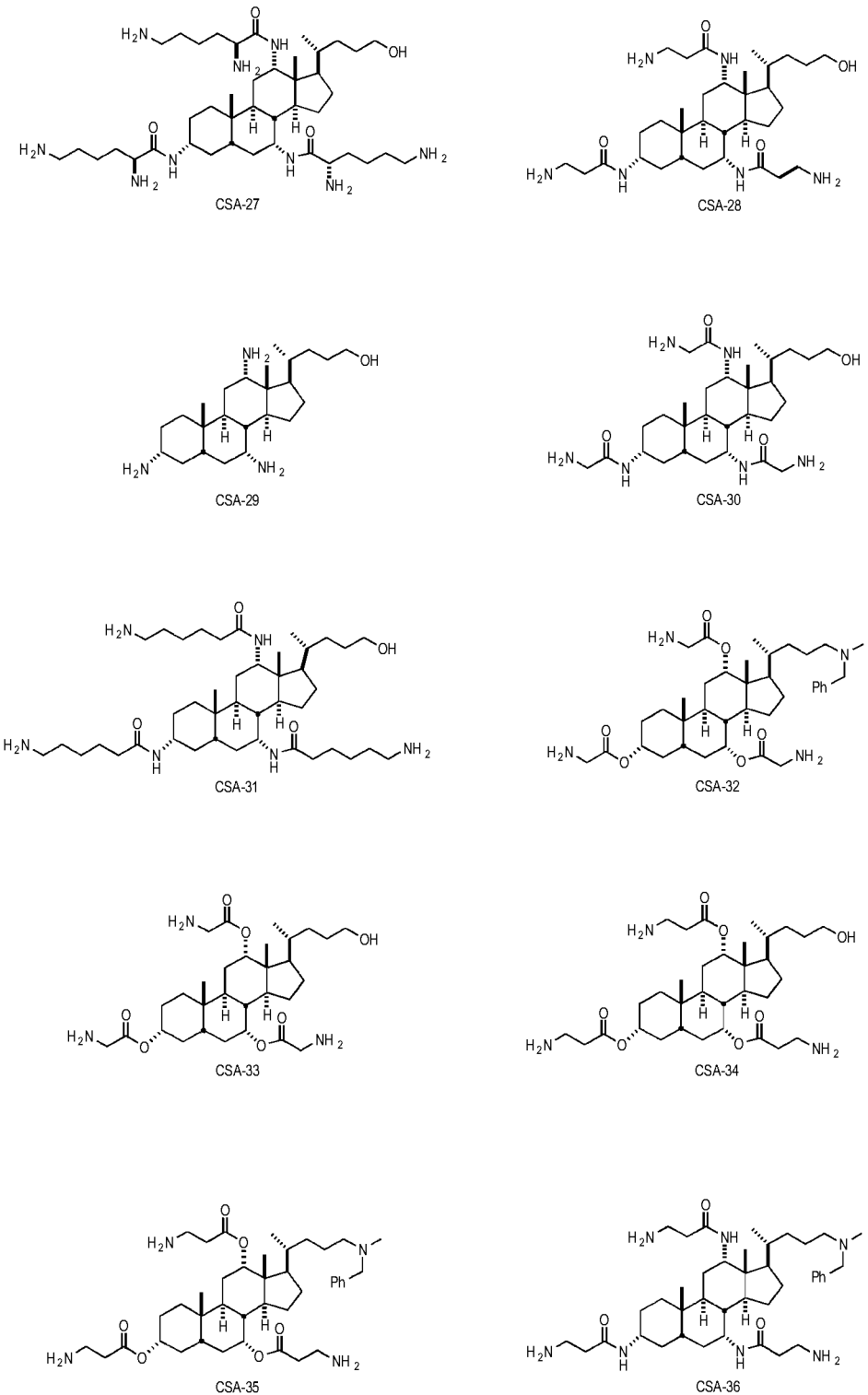
Figure 1A:
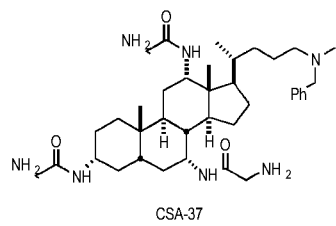
Figure 1A:
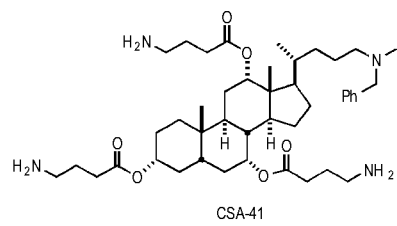
Figure 1A:
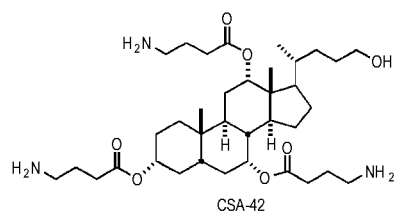
Figure 1A:
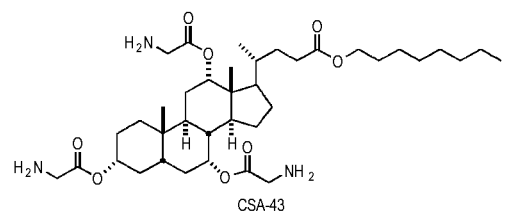
Figure 1A:
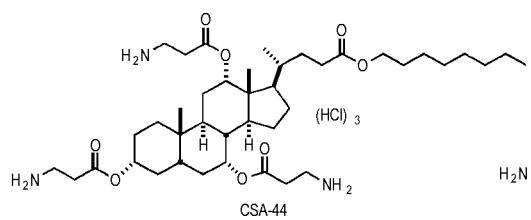
Figure 1A:
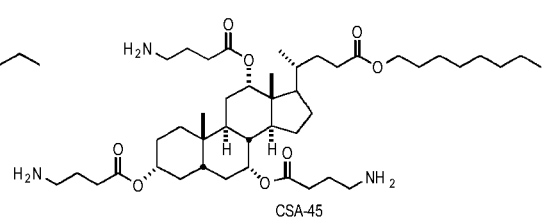
Figure 1A:
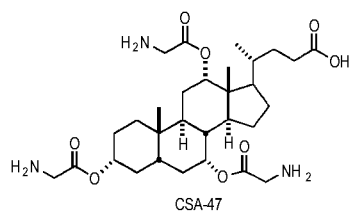
Figure 1A:
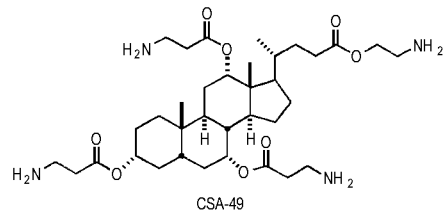
Figure 1A:
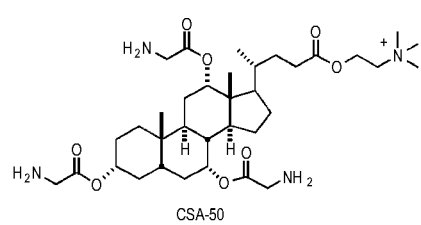
Figure 1A:
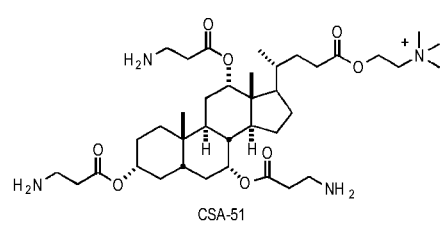
Figure 1A:
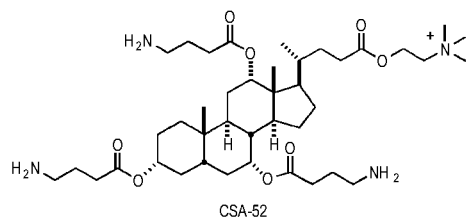
Figure 1A:
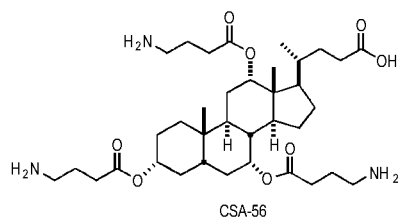
Figure 1A:
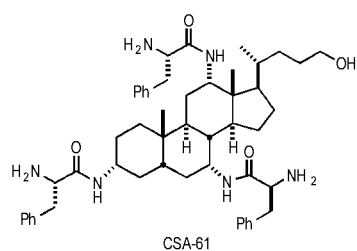
Figure 1A:
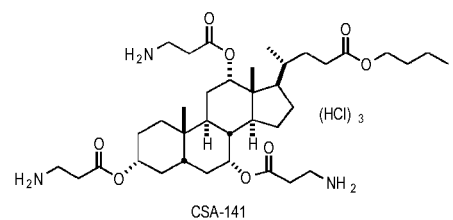
Figure 1A:
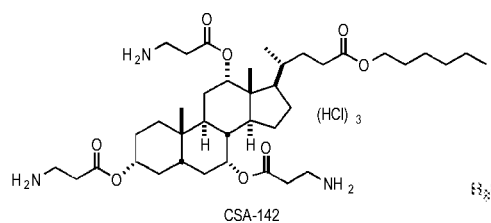
Figure 1A:
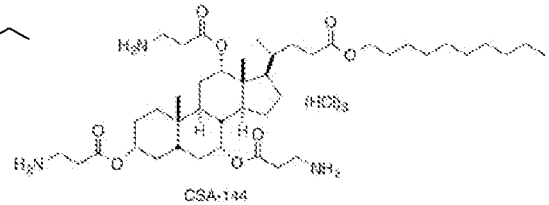
Figure 1A:
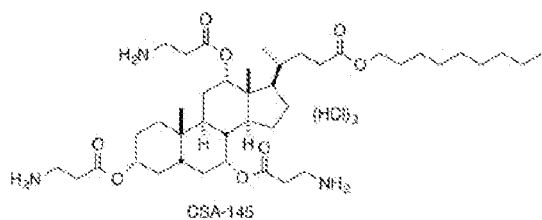
Figure 1A:
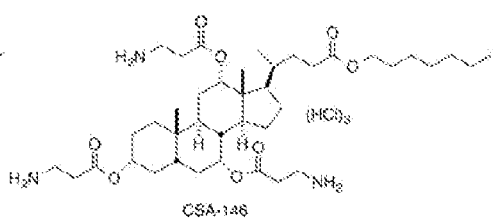
Figure 1A:
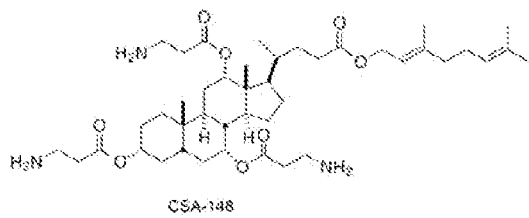

This application claims the benefit of U.S. Provisional Application No. 63/036,413, filed Jun. 8, 2020, which is incorporated by reference in its entirety.

BACKGROUND

Coronaviruses are single stranded, positive sense RNA viruses that cause respiratory diseases in mammals and birds. Coronaviruses have genomes of approximately 26 to 32 kilobases, one of the largest of known RNA viruses. Coronaviruses have characteristic club-shaped spikes that project from an enveloped surface. When coronavirus virions were first visualized under electron microscopy, these spikes created an image reminiscent of a solar corona, and the viruses were named accordingly.

There are multiple different types of coronaviruses capable of infecting humans. Some carry relatively minor risk and are associated with symptoms of the common cold. However, other types of coronaviruses can cause major symptoms. Four human coronaviruses (OC43, HKU1, 229E, and NL63) are known to cause symptoms that are generally mild. These continually circulate in the human population and are believed to cause of about 15% of all common colds.

The three human coronaviruses that can cause potentially severe symptoms are severe acute respiratory syndrome coronavirus (SARS-CoV), Middle East respiratory syndrome-related coronavirus (MERS-CoV), and severe acute respiratory syndrome coronavirus 2 (SARS-CoV-2). SARS first appeared in late 2002 and would go on to infect more than 8,000 people, with a fatality rate of about 10%. MERS first appeared in mid-2012. MERS has a fatality rate of about 35% but does not transmit from human to human as readily as other coronaviruses.

In late 2019, an outbreak of pneumonia in Wuhan, China was traced to a novel coronavirus, which has now become known as SARS-CoV-2. Infection with SARS-CoV-2 can cause coronavirus disease 2019 (COVID-19), with symptoms including fever, cough, fatigue, shortness of breath, organ damage, swelling of extremities, inflammation, and loss of smell and taste. While most cases do not progress beyond such flu-like symptoms, some progress to acute respiratory distress syndrome (ARDS), which can lead to septic shock, blood clots, and multi-organ failure. By early 2020, COVID-19 had become a global pandemic. While SARS-CoV-2 does not have as high of a fatality rate as SARS or MERS, it much more transmissible. There are also several mutations, which may or may not evade existing immunity acquired by exposure to other viruses, such as other coronaviruses.

There are a few recently developed vaccines and antiviral treatments of questionable efficacy for COVID-19. The vaccines are experimental and have not been through full FDA testing for safety and efficacy. The course of most viral infections involves exposure to the virus, development of symptoms, generation of specific adaptive immune responses, and elimination of the virus from the patient. Apart from a safe and effective vaccine, the most effective means of stopping the influence of a wide-spread virus is broad exposure by the population, leading to herd immunity. However, this can be costly in terms of the morbidity it takes to achieve such herd immunity.

Innate immunity, on the other hand, provides continuous protection against pathogens ranging from bacteria to fungi to viruses. The continuity and breadth of activity of innate immunity is important due to constant exposure to a broad array of pathogens. The pathogenesis of coronavirus infection such as a SARS-CoV-2 infection, in some patients, may be considered a failure of innate immunity because such are insufficiently protected by broad innate immunity during the time it takes to develop a specific adaptive immune response.

While there are vaccines, there is still significant aversion by many people due to their still experimental status, with no long-term proof of safety, which may require years of observation and retrospective analysis.

Accordingly, there is an ongoing need for compositions and methods capable of deactivating coronaviruses. Such compositions and methods should be capable of preventing, decreasing, and/or treating a coronavirus infection.

BRIEF SUMMARY

The present disclosure describes methods of administering one or more cationic steroidal antimicrobial (CSA) compounds in order to deactivate coronavirus. Methods disclosed herein are capable of decreasing or inhibiting coronavirus infection or pathogenesis of a cell in vitro, ex vivo, or in vivo.

In one embodiment, a method of deactivating coronavirus comprises: (1) providing a deactivation composition that includes one or more CSA compounds and a carrier; (2) administering the deactivation composition to a subject in need thereof; and (3) the deactivation composition deactivating coronavirus virions in the subject or coming into contact with the subject. The method can thereby prevent, decrease, or inhibit a coronavirus infection, such as COVID-19, of the subject.

The subject may be a mammal or bird. The subject may be a human, livestock animal, pet, laboratory animal, or zoo animal.

The carrier may be any suitable carrier in which the one or more CSA compounds can be mixed. Examples include water, alcohol, other organic solvents, an emulsion, or combinations thereof.

The deactivation composition may be administered via any suitable route of administration including topically, orally, transdermally, via inhalation, or parenterally (e.g., via injection).

In one embodiment, a method of deactivating coronavirus comprises: (1) providing a deactivation composition including one or more CSA compounds in a carrier; (2) applying the deactivation composition to a surface; and (3) the deactivation composition deactivating coronavirus virions on the surface or coming into contact with the surface.

The surface may include any surface believed to be contaminated with coronavirus or believed to be susceptible to or at risk for contamination with coronavirus, and which is amenable to being contacted with a deactivation composition.

In some embodiments, a CSA solution is converted into a fog, which is introduced into a room or building, such as a barn, feedlot, or other animal quarters, or a building where other mammals, including human, may occupy. The fogging of a room widely disperses the CSA compounds so as to contact any exposed or accessible surfaces in the room. In addition, it has been found that animals, including farm animals and other mammals, can safely breath in the fog and become protected against contracting or spreading corona-virus diseases. A nebulizer can be used to deliver a nebulized solution of CSA compounds to a subject, including a human subject, as therapeutic or prophylactic treatment.

Any CSA compound described herein, or any combination of such CSA compounds may be utilized in a treatment composition. Presently preferred CSA compounds include CSA-44, CSA-131, and/or structurally similar CSA compounds.

Additional features and advantages will be set forth in part in the description that follows, and in part will be obvious from the description, or may be learned by practice of the embodiments disclosed herein. It is to be understood that both the foregoing brief summary and the following detailed description are exemplary and not restrictive of the embodiments disclosed herein or as claimed.

BRIEF DESCRIPTION OF THE DRAWINGS

In order to describe various features and concepts of the present disclosure, a more particular description of certain subject matter will be rendered by reference to specific embodiments which are illustrated in the appended drawings. Understanding that these figures depict just example embodiments and are not to be considered to be limiting in scope, various embodiments will be described and explained with additional specificity and detail through the use of the accompanying drawings in which:

FIG. 1A illustrates examples of cationic steroidal antimicrobial compounds having ester or amide linkages at one or more of the $R_3$, $R_7$, and $R_{12}$ positions;

FIG. 1B illustrates examples of cationic steroidal antimicrobial compounds having ether linkages at one or more of the $R_3$, $R_7$, and $R_{12}$ positions; and FIG. 1C illustrate example cationic steroidal antimicrobial compounds having an amide linkage within the $R_{18}$ group and ether or urethane linkages at the $R_3$, $R_7$, and $R_{12}$ positions.

DETAILED DESCRIPTION

I. Overview of CSA Compounds

Cationic steroidal anti-microbial (CSA) compounds, also referred to as “CSA compounds”, “CSAs”, “CSA molecules”, or “ceragenin” compounds, are synthetically produced, small molecule chemical compounds that include a sterol backbone having various charged groups (e.g., amine and cationic groups) attached to the backbone. The sterol backbone can be used to orient amine or guanidine groups on a face or plane of the sterol backbone. CSAs are cationic and amphiphilic, based upon the functional groups attached to the backbone. They are facially amphiphilic with a hydrophobic face and a polycationic face.

Without wishing to be bound to any particular theory, it is theorized that the CSA compounds described herein can act as anti-viral agents by binding to the viral envelope and/or capsid and inserting partially or fully therein, thereby forming a pore that results in the leakage of internal virion materials and/or leads to the disruption of host-binding structures such as glycoproteins to prevent the virion from attaching to host cells.

An example of a CSA compound is shown below as Formula I. As will be discussed in greater detail below, the R groups of Formula I can have a variety of different functionalities, thus providing a given ceragenin compound with specific, different properties. In addition, as will be appreciated by those of skill in the art, the sterol backbone can be formed of 5-member and/or 6-member rings, so that p, q, m, and n may independently be 1 (providing a 6-member ring) or 0 (providing a 5-member ring). Typically, the A, B, and C rings are 6-member rings while the D ring is a 5-member ring.

(I)

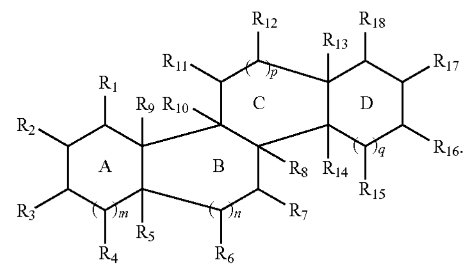

The CSA compounds can have a structure of Formula II, Formula III, or Formula IV:

(II)

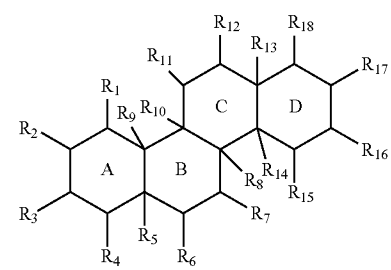

(III)

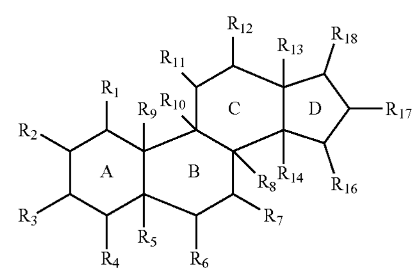

(IV)

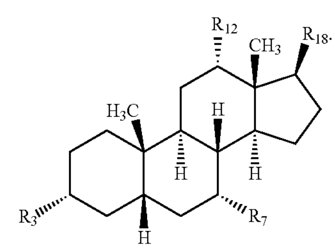

Definitions for the R groups are set forth below. Formula II is a subset of Formula I in which rings A, B, C, and D are 6-member rings. Formula III is a subset of Formula I in which rings A, B, and C are 6-member rings and D is a 5-member ring. Formula IV is a subset of Formula III in which the stereochemistry is defined and the R groups other than $R_3$, $R_7$, $R_{12}$, and $R_{18}$ are defined as either hydrogen or methyl.

A number of examples of CSA compounds of Formula I, Formula II, Formula III, and Formula IV that can be utilized to stimulate stem cells are illustrated in FIGS. 1A-1C.

Typically, CSAs used herein are of two types: (1) CSAs having cationic groups linked to the sterol backbone with hydrolysable linkages and (2) CSAs having cationic groups linked to the sterol backbone with non-hydrolysable linkages. For example, one type of hydrolysable linkage is an ester linkage, and one type of non-hydrolysable linkage is an ether linkage. CSAs of the first type can be "inactivated" by hydrolysis of the linkages coupling the cationic groups to the sterol backbone, whereas CSAs of the second type are more resistant to degradation and inactivation.

Figure 1B:
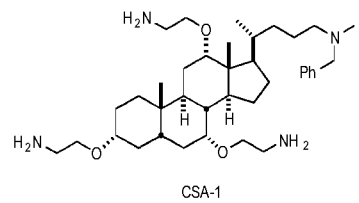
Figure 1B:
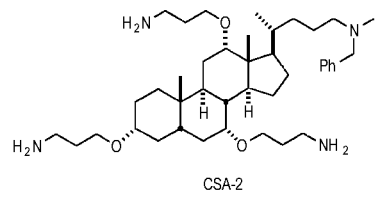
Figure 1B:
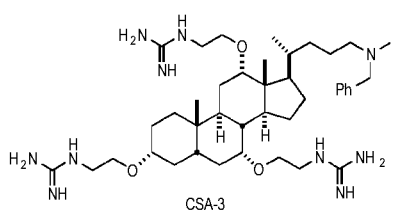
Figure 1B:
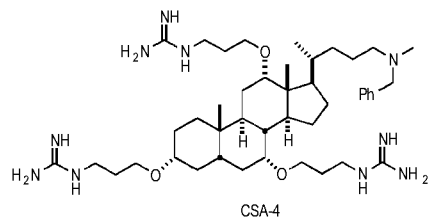
Figure 1B:
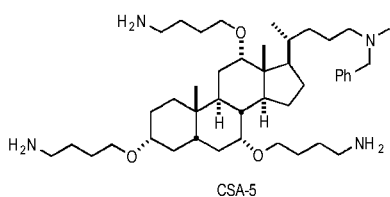
Figure 1B:
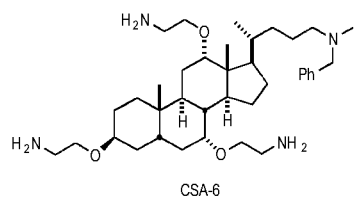
Figure 1B:
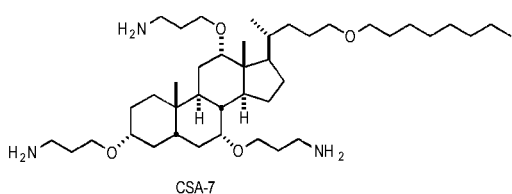
Figure 1B:
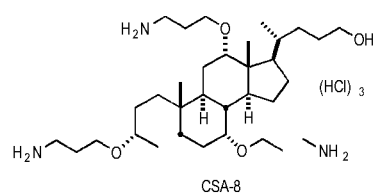
Figure 1B:
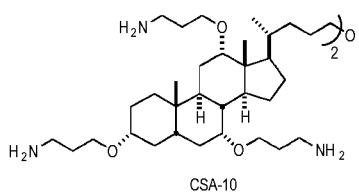
Figure 1B:
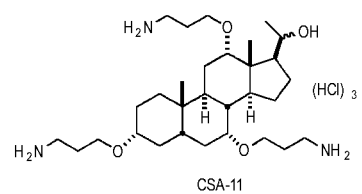
Figure 1B:
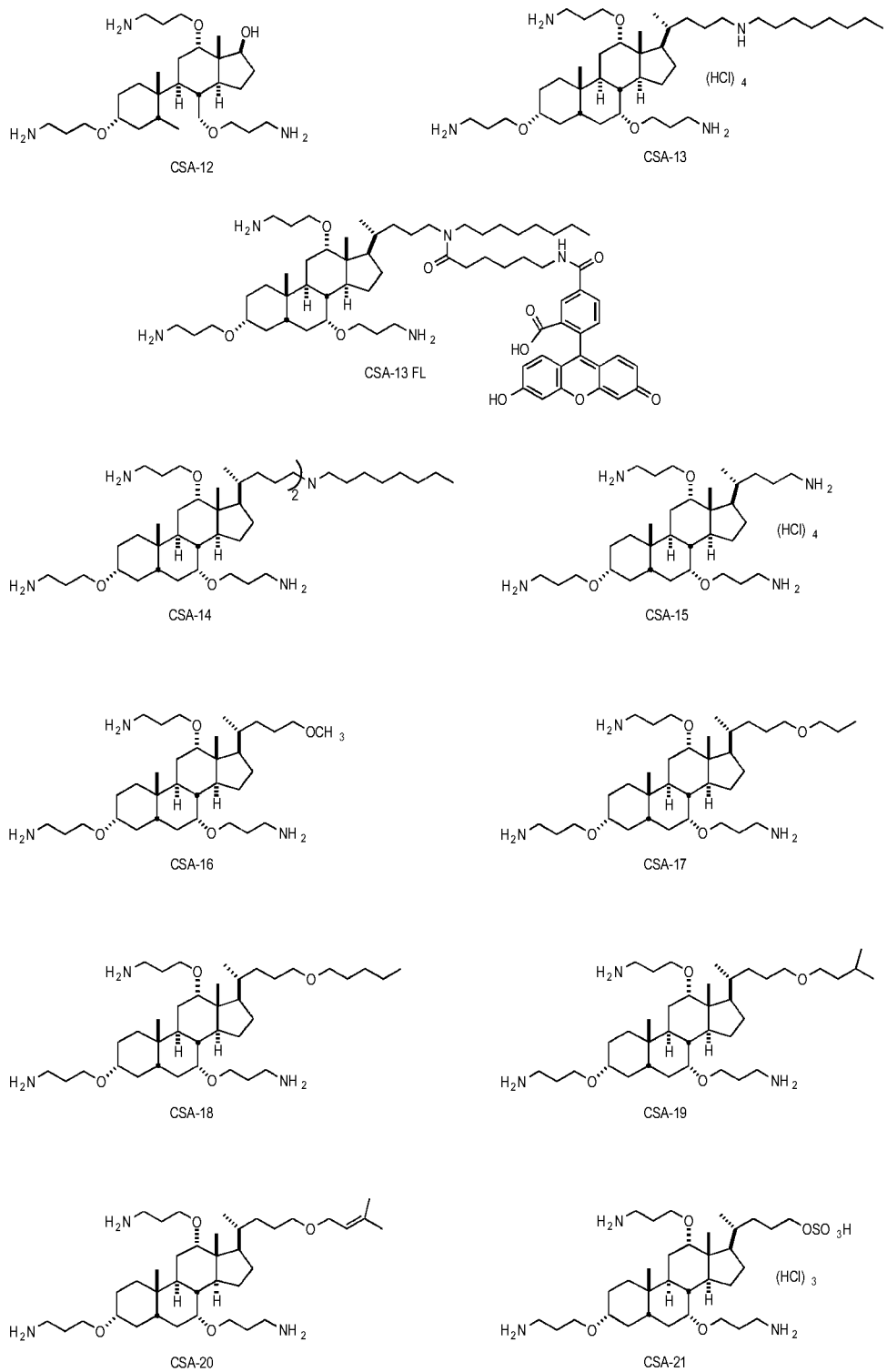
Figure 1B:
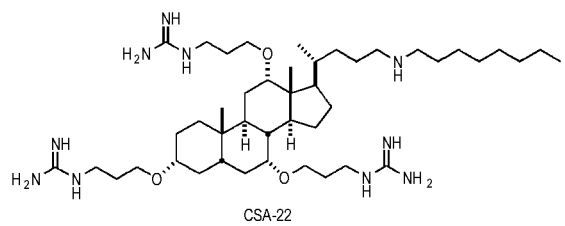
Figure 1B:
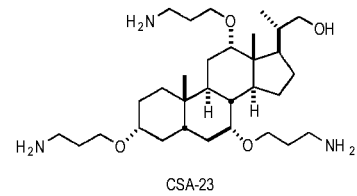
Figure 1B:
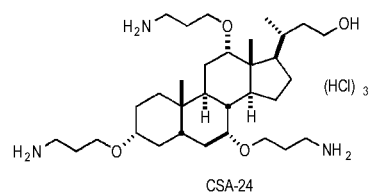
Figure 1B:
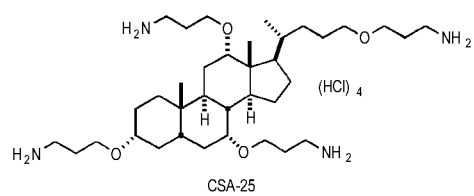
Figure 1B:
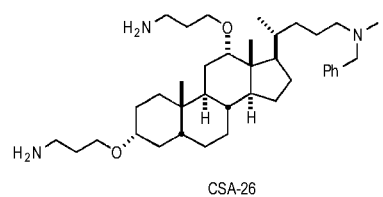
Figure 1B:
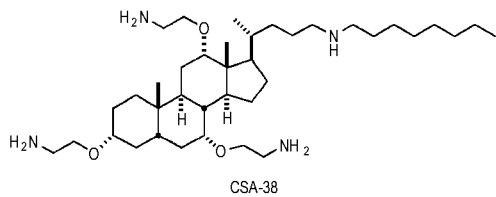
Figure 1B:
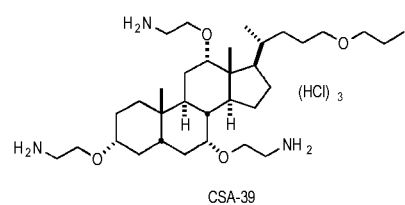
Figure 1B:
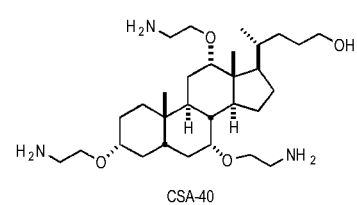
Figure 1B:
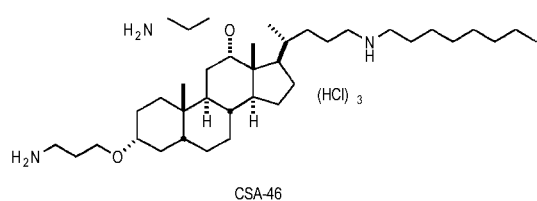
Figure 1B:
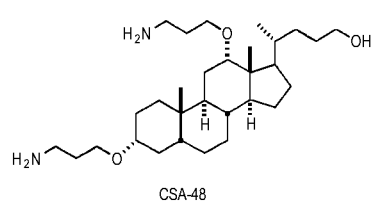
Figure 1B:
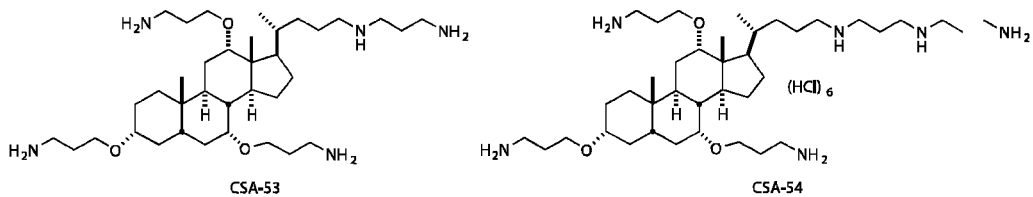
Figure 1B:
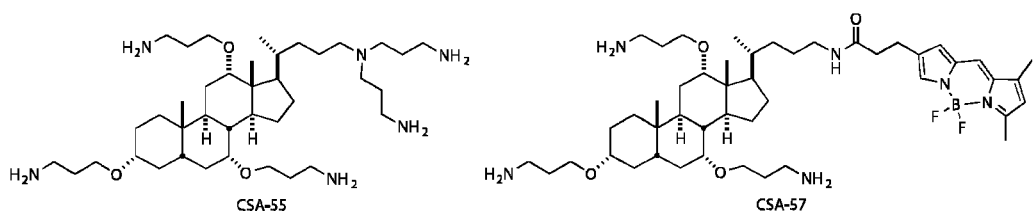
Figure 1B:
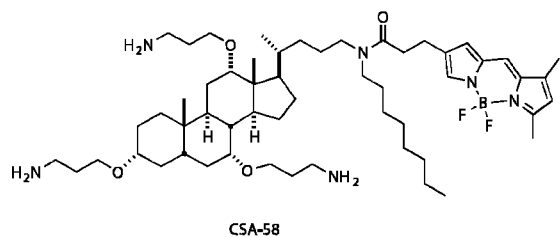
Figure 1B:
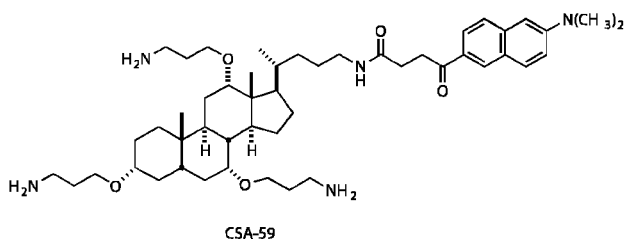
Figure 1B:
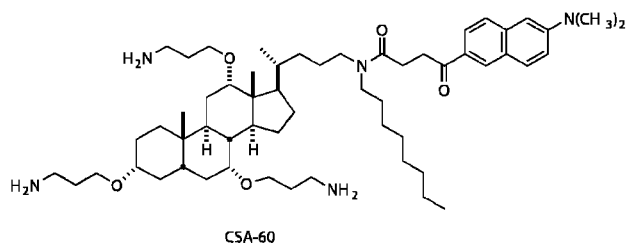
Figure 1B:
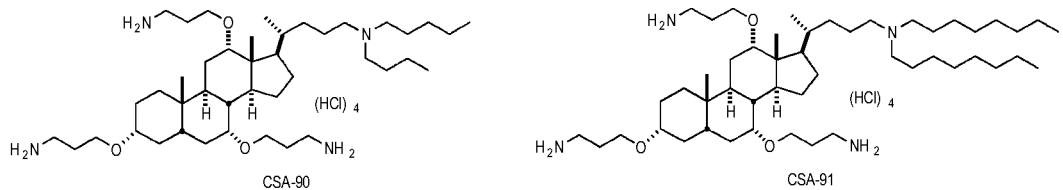
Figure 1B:
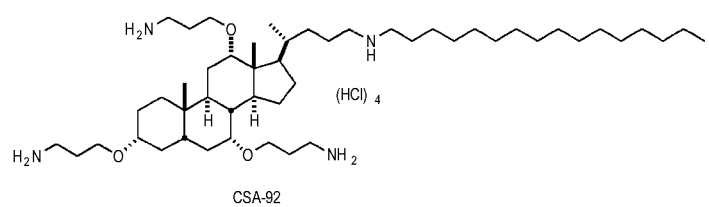
Figure 1B:
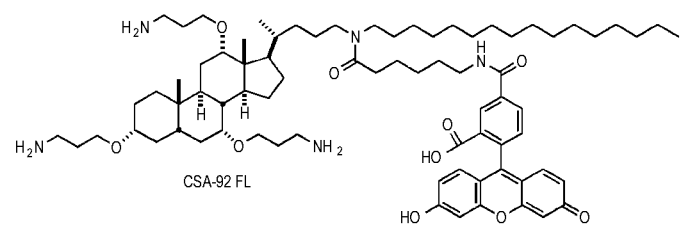
Figure 1B:
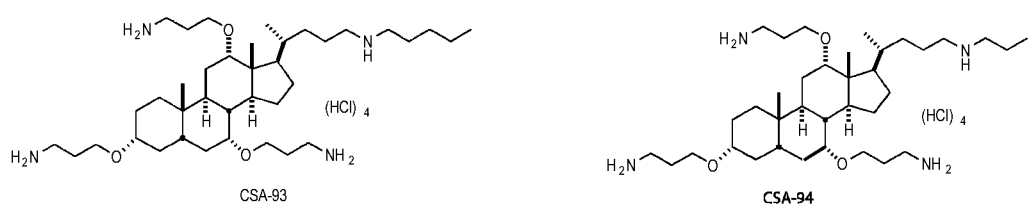
Figure 1B:
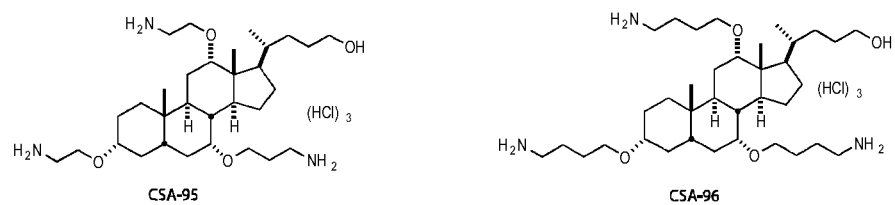
Figure 1B:
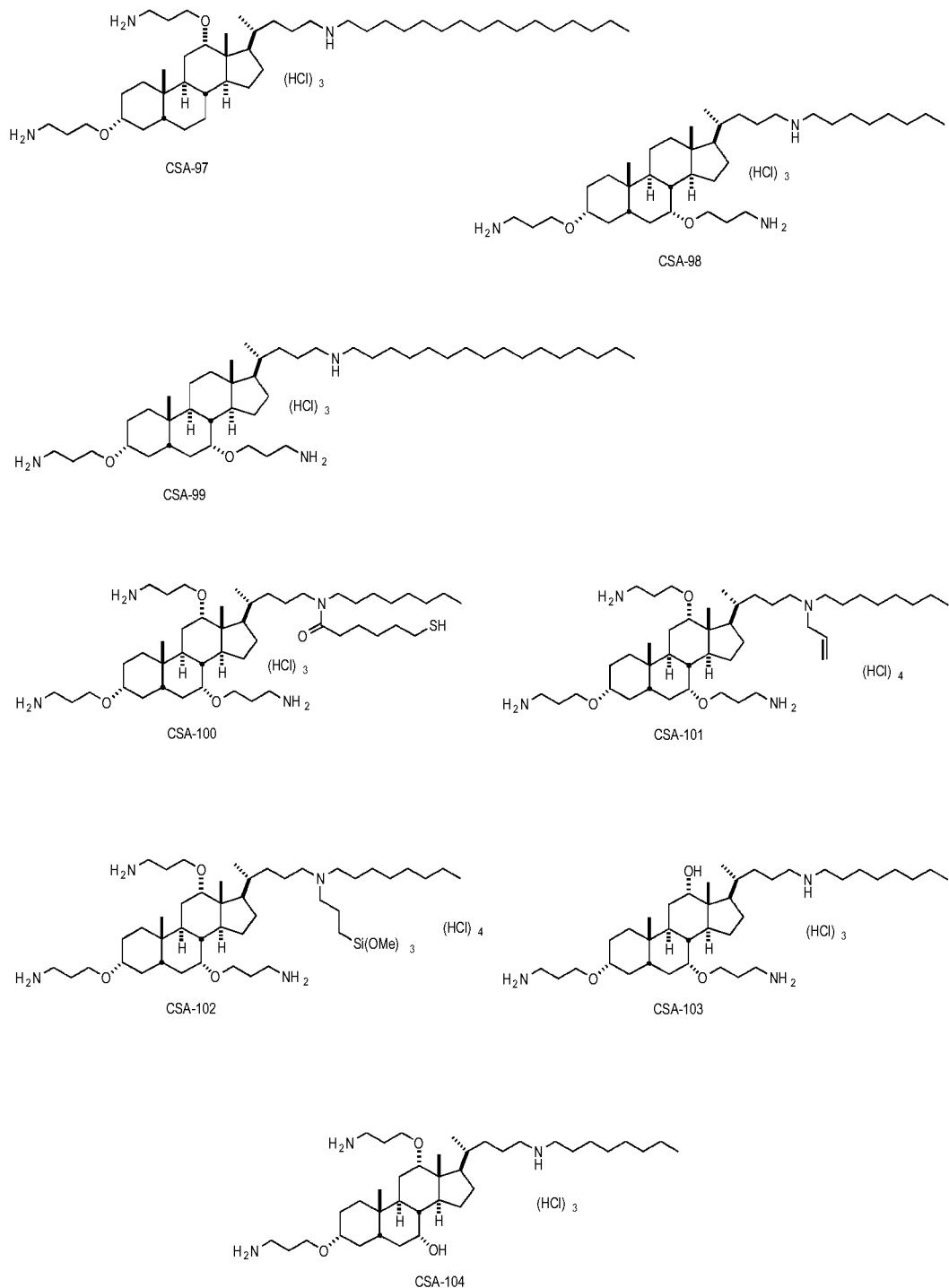
Figure 1B:
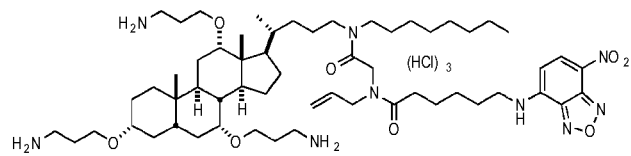
Figure 1B:
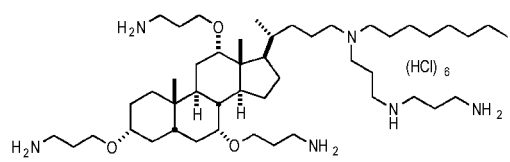
Figure 1B:
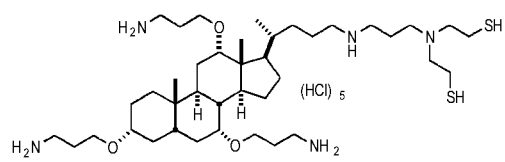
Figure 1B:
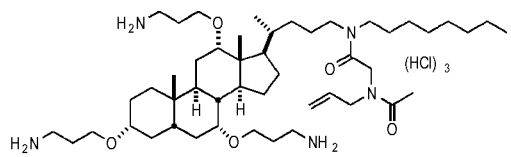
Figure 1B:
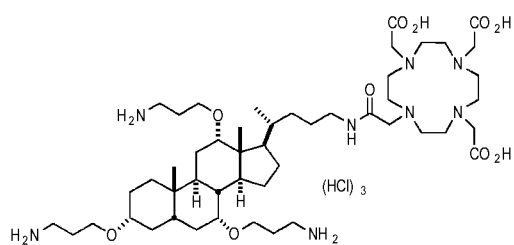
Figure 1B:
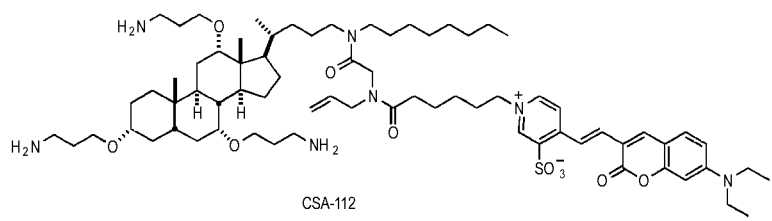
Figure 1B:
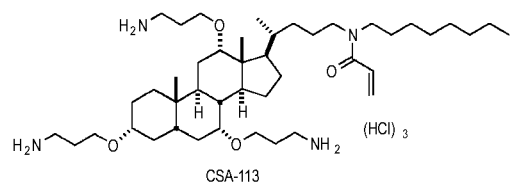
Figure 1B:
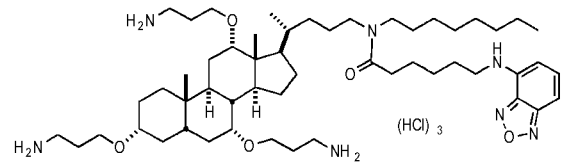
Figure 1B:
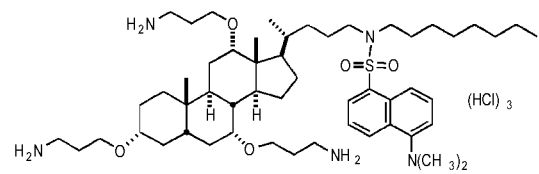
Figure 1B:
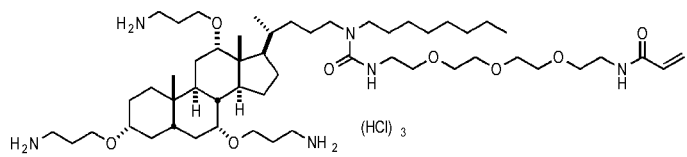
Figure 1B:
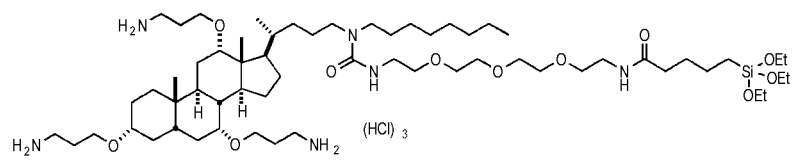
Figure 1B:
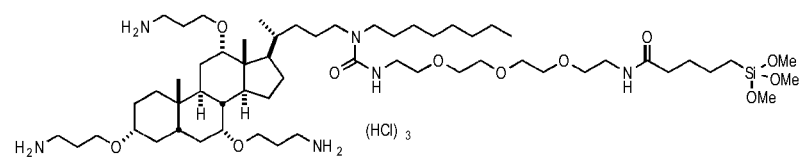
Figure 1B:
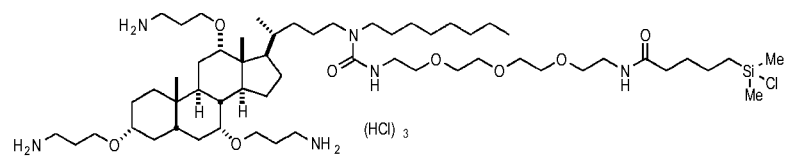
Figure 1B:
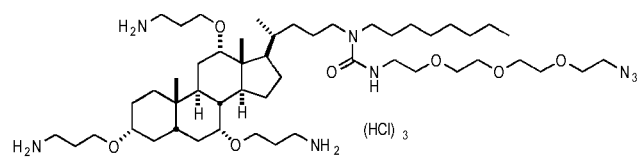
Figure 1B:
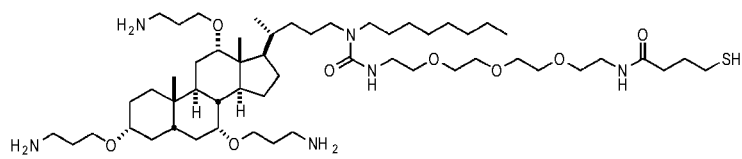
Figure 1B:
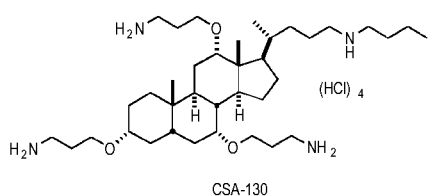
Figure 1B:
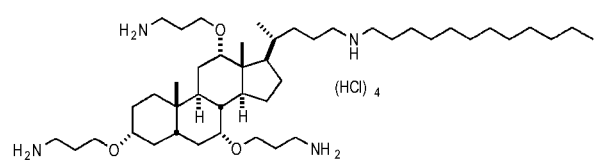
Figure 1B:
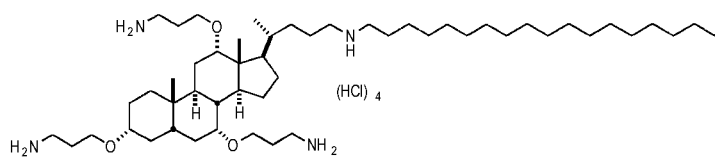
Figure 1B:
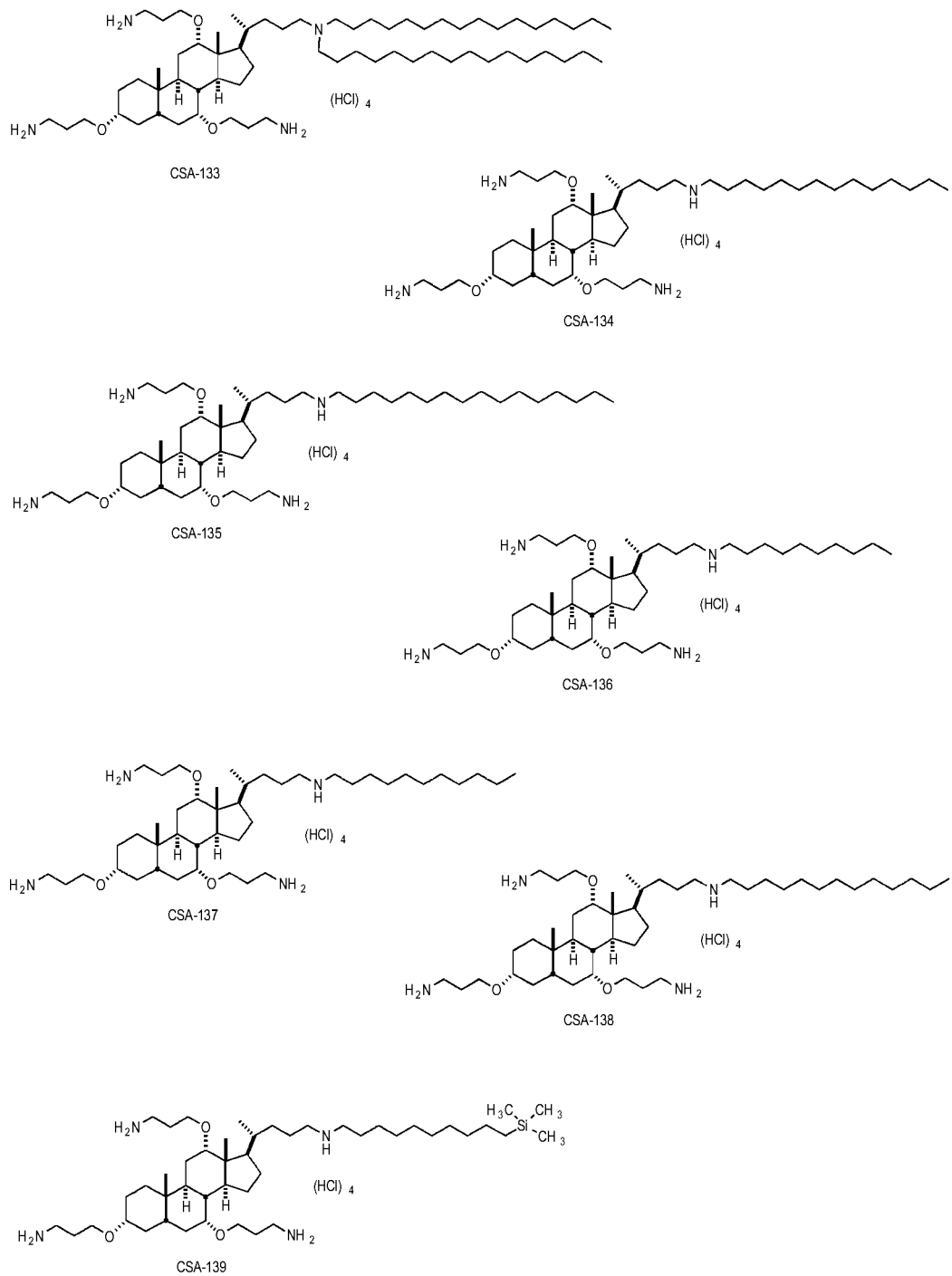
Figure 1C:
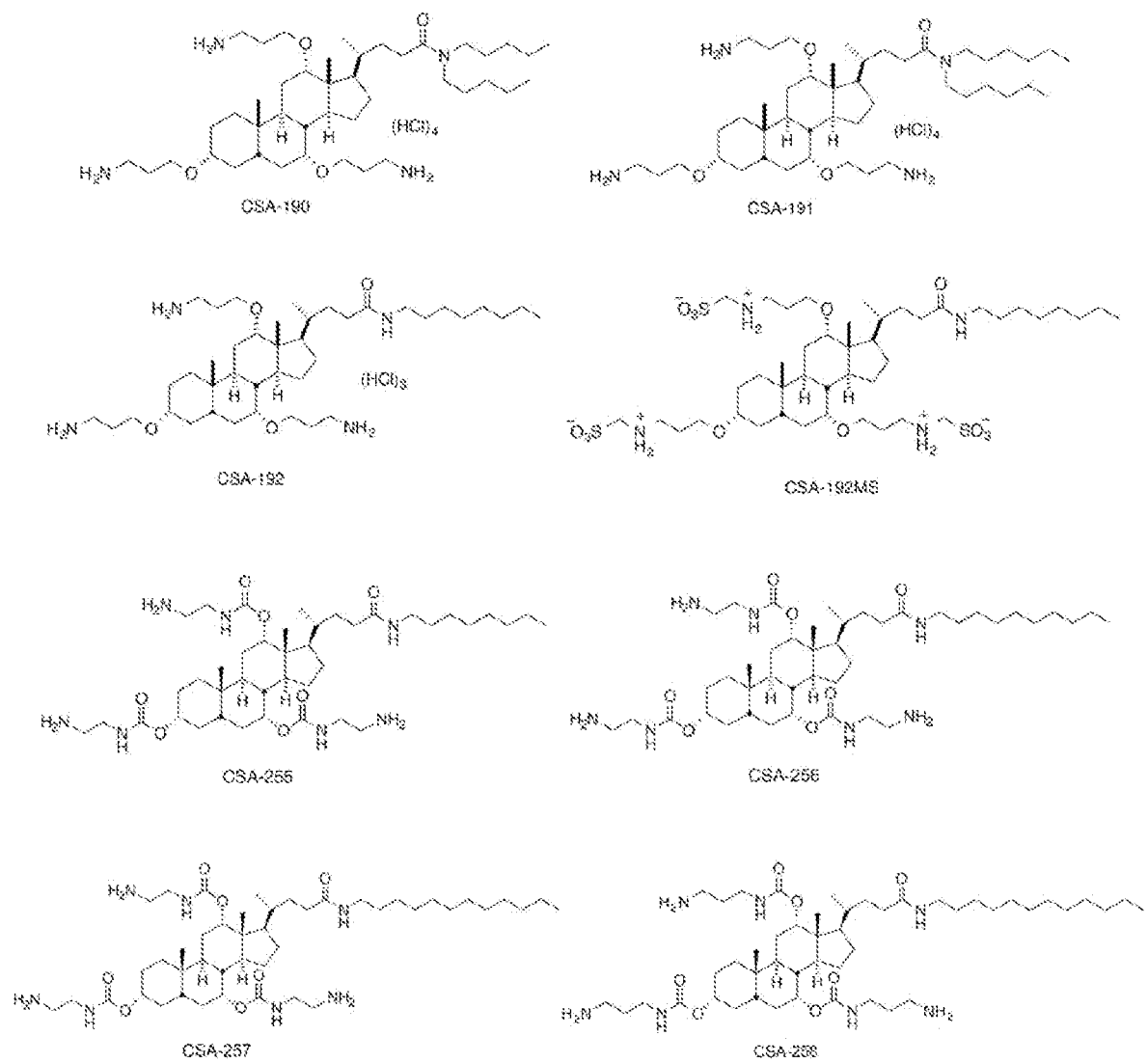

A number of examples of CSA compounds that may be used in the embodiments described herein are illustrated in FIGS. 1A-1C. Non-limiting examples of CSAs with hydrolysable linkages are set forth in FIG. 1A and include CSA-27, CSA-28, CSA-30, CSA-31, CSA-32, CSA-33, CSA-34, CSA-35, CSA-36, CSA-37, CSA-41, CSA-42, CSA-43, CSA-44, CSA-45, CSA-47, CSA-49, CSA-50, CSA-51, CSA-52, CSA-56, CSA-61, CSA-141, CSA-142, CSA-144, CSA-145, CSA-146, and CSA-148.

Non-limiting examples of CSAs with non-hydrolysable linkages are set forth in FIG. 1B and include CSA-13, CSA-90, CSA-131, CSA-136, CSA-137, and CSA-138.

Non-limiting examples of CSAs with both hydrolysable and non-hydrolysable linkages are set forth in FIG. 1C and include CSA-190, CSA-191, CSA-192, CSA-255, CSA-256, and CSA-257.

In presently preferred embodiments, compositions used to deactivate coronaviruses include CSA compounds such as CSA-44, CSA-131, CSA-148, CSA-255, structurally similar CSA compounds, or combinations thereof.

In Formula I, Formula II, Formula III, and Formula IV, at least two of $R_3$, $R_7$, or $R_{12}$ may independently include a cationic moiety attached to the sterol backbone via hydrolysable (e.g., ester) or non-hydrolizable (e.g., ether) linkages. A tail moiety is usually attached to Formula I at $R_{18}$. The tail moiety may be charged, uncharged, polar, nonpolar, hydrophobic, or amphipathic, for example, and can thereby be selected to adjust the properties of the CSA and/or to provide desired characteristics.

The activity of the CSA compounds can be affected by the orientation of the substituent groups attached to the backbone structure. In one embodiment, the substituent groups attached to the backbone structure are oriented on a single face of the CSA compound. Accordingly, each of $R_3$, $R_7$, and $R_{12}$ may be positioned on a single face of Formula I, Formula II, Formula III, and Formula IV. In addition, $R_{18}$ may also be positioned on the same single face.

II. Deactivation of Coronavirus Using CSA Compounds

Though CSAs are known to provide effective antimicrobial activity against a variety of bacteria, fungi, and some types of viruses, it was not known whether CSA compounds had any ability to deactivate coronaviruses. In particular, CSA compounds are known to provide anti-viral activity against poxviruses, herpes viruses, influenza viruses, and HIV viruses. However, each of these viruses have substantially different characteristics than coronaviruses. These differences include dissimilarities in envelope structure, capsid morphology, glycoprotein composition, size, and nucleic acid replication classification.

CSA compounds have been shown to be effective against poxviruses, as described in U.S. Pat. No. 7,754,705. Poxviruses are double-stranded DNA (dsDNA) viruses, putting them in Group I of the Baltimore virus classification system. Poxviruses are enveloped and have a complex capsid structure that is usually brick or oval in shape. Poxviruses are relatively large (about 200 nm×300 nm). Poxviruses carry the genome in a single, linear, double-stranded segment of DNA. The poxvirus genome also encodes its own RNA polymerase, making replication in the cytoplasm of the infected cell possible rather than requiring delivery to the cell nucleus.

CSA compounds have also been shown to be effective against herpes viruses, as described in U.S. Pat. No. 8,211,879. Like poxviruses, herpes viruses are dsDNA viruses in Group I of the Baltimore virus classification system. Herpes viruses are enveloped and have an icosahedral capsid, with several glycoprotein spikes extending from the virion and giving the virion a diameter of about 225 nm.

CSA compounds have also been shown to be effective against influenza viruses, as described in United States Patent Application Publication No. 2007/0191322. Influenza viruses are antisense single-stranded RNA ((−)ssRNA) viruses, putting them in Group V of the Baltimore virus classification system. Influenza viruses are enveloped, and virions are usually ellipsoidal with a size of about 80 to 120 nm in diameter. Some virions can have spherical and filamentous forms, with filamentous forms reaching up to 20 μm in length. Approximately 500 surface spikes extend from the envelope.

CSA compounds have also been shown to be effective against human immunodeficiency (HIV) virus, as described in International Patent Application Pub. No. WO 2007/089907. The HIV virus is a retrovirus with a single-stranded (+strand or sense) RNA virus that uses reverse transcriptase on a DNA intermediate in its lifecycle ((+)ssRNA-RT virus), putting it in Group VI of the Baltimore virus classification system. HIV viruses are enveloped, roughly spherical, with a diameter of about 120 nm. The capsid is conical and houses the RNA along with enzymes needed for development of the virion including reverse transcriptase and integrase.

Unlike the foregoing types of viruses, coronaviruses are single-stranded (+strand or sense) RNA viruses that do not utilize reverse transcriptase ((+)ssRNA viruses), putting them in Group IV of the Baltimore virus classification system. Coronaviruses are enveloped, roughly spherical, and have a capsid with helical symmetry. Coronaviruses have characteristic club-like spikes that project from their surface. The lipid bilayer of the envelope includes envelope (E), spike (S), and membrane (M) structural proteins in an E:S:M ratio of approximately 1:20:300. The envelope diameter is about 85 nm, while the projecting spikes of the virion are about 20 nm long.

Given the general complexity and diversity of different types viruses and, in particular, the very different structural/morphological, compositional, and replicative characteristics of coronaviruses as compared to the other types of viruses known to be susceptible to CSA compounds, it was not predictable whether CSA compounds would also provide sufficient anti-viral activity against coronaviruses. However, despite such distinguishing features of coronaviruses, CSA compounds have now been surprisingly found to be effective in deactivating coronaviruses such as SARS-CoV-2.

In one embodiment, a method of deactivating coronavirus comprises: (1) providing a deactivation composition that includes one or more CSA compounds and a carrier; (2) administering the deactivation composition to a subject in need thereof; and (3) the deactivation composition deactivating coronavirus virions associated with the subject or coming into contact with the subject. The method can thereby prevent, decrease, or inhibit a coronavirus infection, such as COVID-19, of the subject.

The subject may be a mammal or bird. The subject may be a human, livestock animal, pet, laboratory animal, or zoo animal, for example.

The carrier may be any suitable carrier in which the one or more CSA compounds can be mixed. Examples include water, alcohol and/or other organic solvents, an emulsion, excipients, or combinations thereof. The deactivation composition may be administered via any suitable route of administration including topically, orally, transdermally, via inhalation, or via injection. Additional details regarding carriers, pharmaceutical compositions, and routes of administration are provided in another section below, though a few presently preferred embodiments are briefly described.

In some embodiments, the composition is formulated as a cream, liniment, salve, lotion, liquid solution, spray, soap, or other such formulation readily administrable in a topical application. Topical administration can beneficially provide effective and long-lasting protection against viral transmission through skin contact. This can include direct inoculation (e.g., when a subject's hands are contaminated and the subject touches his/her face), spreading of virions from skin to surfaces (e.g., door handles), and spreading of virions from one person's skin to another person's skin (e.g., during a handshake).

In some embodiments, the composition is formulated as an aqueous solution capable of being nebulized by a nebulizer, or as a powder capable of delivery via an inhaler, or in some other form suitable for delivery via inhalation. Inhalation of the deactivation composition can beneficially prevent or reduce viral infection of airway cells such as epithelial cells. Inhalation can also beneficially treat the respiratory system of a subject already infected with coronavirus by deactivating virions already present in the respiratory system and/or by reducing the ability of virions to propagate and infect other cells of the respiratory system.

The treatment composition may be administered using any suitable inhalation route, including through the use of a metered-dose inhaler, a nebulizer, and/or a dry powder dispersion device. These types of devices typically include a mouthpiece or facemask enabling transfer of nebulized/atomized medicament to the patient. A nebulizer may be an ultrasonic nebulizer, a jet nebulizer, a vibrating mesh nebulizer, or a soft mist inhaler, for example.

In some embodiments, such as those associated with delivery via inhalation, the carrier comprises a saline solution. The carrier may optionally include one or more excipients suitable for use in an inhalation application. Suitable excipients include, for example, inhalable bulking powders, carbohydrates such as monosaccharides (e.g., glucose, arabinose), disaccharides (e.g., lactose, saccharose, maltose), and oligo- and polysaccharides (e.g., dextran, cyclodextrins), alcohols and polyalcohols (e.g., ethanol, sorbitol, mannitol, xylitol), salts (e.g., sodium chloride, calcium carbonate, carboxylic acid salts, fatty acid salts), amino acids (e.g., glycine), buffers (e.g., citrate, phosphate, acetate), or combinations thereof.

In another embodiment, a method of deactivating coronavirus comprises: (1) providing a deactivation composition including one or more CSA compounds in a carrier; (2) applying the deactivation composition to a surface; and (3) the deactivation composition deactivating coronavirus virions on the surface or coming into contact with the surface.

The surface may include any surface believed to be contaminated with coronavirus or believed to be susceptible to or at risk for contamination with coronavirus, and which is amenable to being contacted with a deactivation composition.

For example, the surface may be located in a medical environment such as a hospital, doctor's office, clinic, laboratory, quarantine center, or the like. The surface may be located in a household environment, work environment (e.g., office, factory), gathering place (e.g., theater, arena, stadium, classroom, church), or place of business (e.g., store, restaurant), for example. The surface may be located in an environment where mammals and/or birds are held and/or processed, such as a farm, dairy, ranch, horse facility, livestock facility, poultry operation, meat processing facility, slaughterhouse, butcher shop, or an animal market, for example.

In embodiments, a deactivation composition is applied in a relatively short or temporary regimen until the subject has sufficiently recovered from an infection or is believed to no longer be at risk of contracting an infection.

In other embodiments, a deactivation composition is applied in a more continuous manner. For example, the deactivation composition may be applied prophylactically to at-risk subjects such as medical professionals or those known to have had contact with an infected individual. In such circumstances, the deactivation composition may be administered multiple times a day (e.g., morning and night), daily, weekly, or at a frequency suitable to provide sufficient protection to the subject.

One method of application to a surface and/or subject includes providing a deactivation composition in a form suitable for fogging. An environment to be treated (such as any of the exemplary environments described above) may be exposed to the fog and surfaces within the environment are thereby exposed to the deactivation composition.

In some applications, one or more subjects may be present in the environment during fogging or soon thereafter and are allowed to breathe the deactivation composition. This method may be particularly useful in animal facilities, for example, as a method for simultaneously applying the deactivation composition to surfaces and administering the deactivation composition to the animals.

In some embodiments, the one or more CSA compounds are included by weight in the deactivation composition at about 0.01%, 0.1%, 0.2%, 0.3%, 0.5%, 1%, 2%, 3%, 5%, 10%, 15%, 20%, 25%, or 30%, or are included by weight within a range defined by any two of the foregoing percentage values. In some embodiments, the one or more CSA compounds are included at a concentration of about 1 µg/ml, 5 µg/ml, 10 µg/ml, 25 µg/ml, 50 µg/ml, 100 µg/ml, 150 µg/ml, or 200 µg/ml, or are included at a concentration within a range defined by any two of the foregoing concentration values.

It will be understood that in the foregoing examples, the upper concentration endpoints do not necessarily represent a lack of effectiveness at CSA concentrations beyond the upper endpoints. Rather, the upper range endpoints define ranges for which effective activity may be achieved without the need for additional CSA compounds, thereby providing efficient use of CSA compounds given the associated formulation costs. In some implementations, such as where costs are less important than providing greater activity, the one or more CSA compounds may be included at concentrations higher than the foregoing ranges.

Any CSA compound described herein, or any combination of such CSA compounds, may be utilized in a deactivation composition. In some circumstances, it may be preferable to administer one or more CSA compounds having hydrolysable linkages. Exemplary compounds include CSA-27, CSA-28, CSA-29, CSA-30, CSA-31, CSA-32, CSA-33, CSA-34, CSA-35, CSA-36, CSA-37, CSA-41, CSA-42, CSA-43, CSA-44, CSA-45, CSA-47, CSA-49, CSA-50, CSA-51, CSA-52, CSA-56, CSA-61, CSA-141, CSA-142, CSA-144, CSA-145, CSA-146, and CSA-148, in particular CSA-44, CSA-142, CSA-144, and CSA-148. These will be hydrolyzed more rapidly than CSA compounds with non-hydrolysable linkages and may therefore carry less risk of staying too long in active form within the system of the subject or on a surface.

On the other hand, in certain situations may be preferable to utilize one or more CSA compounds with non-hydrolysable linkages where longer term protection is desired and/or carries less risk, such as when a deactivation composition is applied to a surface for purposes of disinfection. Exemplary compounds include CSA-1, CSA-26, CSA-38, CSA-40, CSA-46, CSA-48, CSA-53, CSA-55, CSA-57, CSA-60, CSA-90, CSA-107, CSA-109, CSA-110, CSA-112, CSA-113, CSA-118, CSA-124, CSA-130, CSA-131, CSA-139, CSA-190, CSA-191, CSA-192, and CSA-255.

III. Example

Virucidal activity of CSA-44 and CSA-131 were tested against SARS-CoV-2 after 30 minutes of contact at 22±2° C. results are tabulated in Table 1.

TABLE 1

Virucidal activity of CSA-44HC1 and CSA-131HC1 against SARS-Cov-2 after a 30-minute contact time at 22 ± 2° C.

| Sample | Concentration (μg/mL) | Virus (CCID$_{50}$/0.1 mL)[a] | LRV[b] |
|---|---|---|---|
| CSA-44HC1 | 100 | 1.2 ± 0.94**** | 3.2 |
| CSA-44HC1 | 25 | 0.8 ± 0.19**** | 3.6 |
| CSA-44HC1 | 5 | 3.9 ± 0.17 | 0.5 |
| CSA-44HC1 | 1 | 4.4 ± 0.12 | 0 |
| CSA-131HC1 | 100 | <1.7**** | >2.7 |
| CSA-131HC1 | 25 | 1.2 ± 0.54**** | 3.2 |
| CSA-131HC1 | 5 | 4.1 ± 0.17 | 0.3 |
| CSA-131HC1 | 1 | 4.1 ± 0.40 | 0.3 |
| Ethanol | 35% | 0.8 ± 0.23**** | 3.6 |
| Virus Control | N/A | 4.4 ± 0.12 | — |

[a] Average of 3 replicates ± standard deviation
[b] LRV (log reduction value) is the log$_{10}$ reduction of virus compared to the virus control
[c] Toxicity was observed in the top dilution (1/10) and therefore the limit of detection of virus was 1.7 log10 CCID50 per 0.1 mL
****$P < 0.0001$ by one-way ANOVA with Dunnett's multiple comparison test, compared with untreated virus control (water).

The data illustrate that CSA compounds were able to provide significant reduction of virus compared to the control. Concentrations of 25 ppm or more showed efficacy on par with 35% ethanol. Although lower, some efficacy was also shown at a lower concentration of 5 ppm. Given the current lack of reliable treatments for Covid-19, such results are surprising and unexpected.

IV. Additional Details of Pharmaceutical Compositions

While CSA compounds described herein can be administered alone, it may be preferable to formulate the compounds as pharmaceutical compositions (i.e., formulations). A pharmaceutical composition is any composition that may be administered in vitro or in vivo or both to a subject in order to treat or ameliorate a condition. In a preferred embodiment, a pharmaceutical composition may be administered in vivo. A subject may include one or more cells or tissues, or organisms. In exemplary embodiments, the subject is an animal. In embodiments, the animal is a mammal. The mammal may be a human or primate in some embodiments. A mammal includes any mammal, such as by way of non-limiting example, cattle, pigs, sheep, goats, horses, camels, buffalo, bison, cats, dogs, rats, mice, bats, pangolins, and humans.

"Pharmaceutically acceptable" and "physiologically acceptable" mean a biologically compatible formulation, gaseous, liquid or solid, or mixture thereof, which is suitable for one or more routes of administration, in vivo delivery, or contact. A formulation is compatible in that it does not destroy activity of an active ingredient therein (e.g., a CSA compound), or induce adverse side effects that far outweigh any prophylactic or therapeutic effect or benefit.

Pharmaceutical compositions may be formulated with a pharmaceutically acceptable excipient, such as a carrier, solvent, stabilizer, adjuvant, diluent, etc., depending upon the particular mode of administration and dosage form. The pharmaceutical compositions can be formulated to achieve a physiologically compatible pH, and may range from about 3 to 11, preferably about 3 to 7, depending on the formulation and route of administration. In alternative embodiments, the pH is adjusted to about 5 to 8. The pharmaceutical compositions may comprise a therapeutically or prophylactically effective amount of at least one compound as described herein, together with one or more pharmaceutically acceptable excipients.

The pharmaceutical composition may comprise a combination of compounds described herein and/or may include a second active ingredient useful in the treatment or prevention of bacterial infection (e.g., anti-bacterial or anti-microbial agents).

The composition can be formulated as a coating, such as on a medical device. In embodiments, the coating is on a medical instrument.

Formulations for parenteral or oral administration can be solids, liquid solutions, emulsions or suspensions. Inhalable formulations for pulmonary administration can be liquids or powders. A pharmaceutical composition can be formulated as a lyophilized solid that is reconstituted with a physiologically compatible solvent prior to administration. Alternative pharmaceutical compositions may be formulated as syrups, creams, ointments, tablets, etc.

Compositions may contain one or more excipients. Pharmaceutically acceptable excipients are determined in part by the particular composition being administered as well as by the particular method used to administer the composition. There exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are pharmaceutically acceptable excipients.

Pharmaceutical compositions may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

Pharmaceutical compositions can be formulated as a suspension comprising a CSA compound in admixture with at least one pharmaceutically acceptable excipient suitable for the manufacture of a suspension.

Pharmaceutical compositions can be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcellulose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxyethanol), a condensation product of ethylene oxide with a partial ester derived from a fatty acid and a hexitol anhydride (e.g., polyoxyethylene sorbitan monooleate); polysaccharides and polysaccharide-like compounds (e.g. dextran sulfate); glycoaminoglycans and glycosaminoglycan-like compounds (e.g., hyaluronic acid); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

Pharmaceutical compositions may be in the form of oil-in water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Pharmaceutical compositions may be in the form of a sterile injectable preparation, such as a sterile injectable aqueous emulsion or oleaginous suspension. The emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propandiol.

Sterile injectable preparations may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose, any bland fixed oil may be employed including synthetic mono- or diglycerides. In addition, fatty acids such as oleic acid may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to 60% of the total volume. In one embodiment, the active compound is dissolved in DMSO and diluted with water.

Pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, and complexation.

Many therapeutics have undesirably short half-lives and/or undesirable toxicity. Thus, the concept of improving half-life or toxicity is applicable to various treatments and fields. Pharmaceutical compositions can be prepared, however, by complexing the therapeutic with a biochemical moiety to improve such undesirable properties. Proteins are a particular biochemical moiety that may be complexed with a CSA for administration in a wide variety of applications. In some embodiments, one or more CSAs are complexed with a protein. In some embodiments, one or more CSAs are complexed with a protein to increase the CSA's half-life. In other embodiments, one or more CSAs are complexed with a protein to decrease the CSA's toxicity. Albumin is a particularly preferred protein for complexation with a CSA. In some embodiments, the albumin is fat-free albumin.

With respect to the CSA therapeutic, the biochemical moiety for complexation can be added to the pharmaceutical composition as 0.25, 0.5, 0.75, 1, 1.5, 2, 2.5, 3, 3.5, 4, 4.5, 5, 10, 20, 50, or 100 weight equivalents, or a range bounded by any two of the aforementioned numbers, or about any of the numbers. In embodiments, the weight ratio of albumin to CSA is about 18:1 or less, such as about 9:1 or less. In embodiments, the CSA is coated with albumin.

Non-biochemical compounds can be added to the pharmaceutical compositions to reduce the toxicity of the therapeutic and/or improve the half-life. Suitable amounts and ratios of an additive that can reduce toxicity can be determined via a cellular assay. With respect to the CSA therapeutic, toxicity reducing compounds can be added to the pharmaceutical composition as 0.25, 0.5, 0.75, 1, 1.5, 2, 2.5, 3, 3.5, 4, 4.5, 5, 10, 20, 50, or 100 weight equivalents, or a range bounded by any two of the aforementioned numbers, or about any of the numbers. In embodiments, the toxicity reducing compound is a cocoamphodiacetate such as Miranol® (disodium cocoamphodiacetate). In embodiments, the toxicity reducing compound is an amphoteric surfactant. In embodiments, the toxicity reducing compound is a surfactant. In embodiments, the molar ratio of cocoamphodiacetate to CSA is between about 8:1 and 1:1, preferably about 4:1. In embodiments, the toxicity reducing compound is allantoin.

In embodiments, a CSA composition is prepared utilizing one or more surfactants. In specific embodiments, the CSA is complexed with one or more poloxamer surfactants. Poloxamer surfactants are nonionic triblock copolymers composed of a central hydrophobic chain of polyoxypropylene (poly(propylene oxide)) flanked by two hydrophilic chains of polyoxyethylene (poly(ethylene oxide)). In some embodiments, the poloxamer is a liquid, paste, or flake (solid). Examples of suitable poloxamers include those by the trade names Synperonics, Pluronics, or Kolliphor. In some embodiments, one or more of the poloxamer surfactant in the composition is a flake poloxamer. In embodiments, the one or more poloxamer surfactant in the composition has a molecular weight of about 3600 g/mol for the central hydrophobic chain of polyoxypropylene and has about 70% polyoxyethylene content. In embodiments, the ratio of the one or more poloxamer to CSA is between about 50 to 1; about 40 to 1; about 30 to 1; about 20 to 1; about 10 to 1; about 5 to 1; about 1 to 1; about 1 to 10; about 1 to 20; about 1 to 30; about 1 to 40; or about 1 to 50. In embodiments, the ratio of the one or more poloxamer to CSA is between 50 to 1; 40 to 1; 30 to 1; 20 to 1; 10 to 1; 5 to 1; 1 to 1; 1 to 10; 1 to 20; 1 to 30; 1 to 40; or 1 to 50. In embodiments, the ratio of the one or more poloxamer to CSA is between about 50 to 1 to about 1 to 50. In embodiments, the ratio of the one or more poloxamer to CSA is between about 30 to 1 to about 3 to 1. In some embodiments, the poloxamer is Pluronic F127.

The amount of poloxamer may be based upon a weight percentage of the composition. In embodiments, the amount of poloxamer is about 10%, 15%, 20%, 25%, 30%, 35%, 40%, about any of the aforementioned numbers, or a range bounded by any two of the aforementioned numbers or the formulation. In embodiments, the one or more poloxamer is between about 10% to about 40% by weight of a formulation administered to the patient. In some embodiments, the one or more poloxamer is between about 20% to about 30% by weight of the formulation. In embodiments, the formulation contains less than about 50%, 40%, 30%, 20%, 10%, 5%, or 1% of CSA. In embodiments, the formulation contains less than about 20% by weight of CSA. The above described poloxamer formulations are particularly suited for the methods of treatment, device coatings, preparation of unit dosage forms (i.e., solutions, mouthwashes, injectables), etc.

In embodiments, the compounds described herein may be formulated for oral administration in a lipid-based formulation suitable for low solubility compounds. Lipid-based formulations can generally enhance the oral bioavailability of such compounds.

A pharmaceutical composition may comprise a therapeutically or prophylactically effective amount of a compound described herein, together with at least one pharmaceutically acceptable excipient selected from the group consisting of medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In embodiments, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the embodiments in the composition.

V. Additional Details of CSA Compounds

Exemplary CSA compounds and methods for their manufacture are described in U.S. Pat. Nos. 6,350,738, 6,486,148, 6,767,904, 7,598,234, 7,754,705, 8,691,252, 8,975,310, 9,434,759, 9,527,883, 9,943,614, 10,155,788, 10,227,376, 10,370,403, and 10,626,139, U.S. Pat. Pub. Nos. 2016/0311850 and 2017/0210776, and U.S. Prov. Pat. App. Nos. 63/025,255 and 63/028,249, which are incorporated herein by reference. The skilled artisan will recognize the compounds within the generic formulae set forth herein and understand their preparation in view of the references cited herein and the Examples.

CSA compounds can have a structure of Formula I, Formula II, Formula III, and/or Formula IV. Formula III differs from Formula I and II by omitting $R_{15}$ and the ring carbon to which it is attached. Formula IV more particularly defines Formula III with respect to stereochemistry and R groups for all but $R_3$, $R_7$, $R_{12}$, and $R_{18}$.

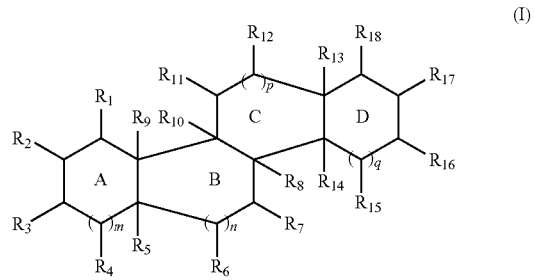

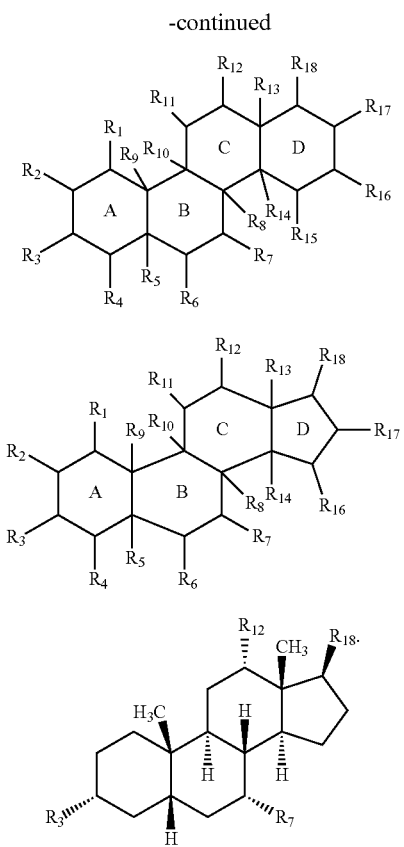

In embodiments of Formulas I, II, III, and IV, at least two of $R_3$, $R_7$, and $R_{12}$ may independently include a cationic moiety (e.g., amino or guanidino groups) bonded to the steroid backbone structure via a hydrolysable or non-hydrolysable linkage. For the embodiments of the present disclosure, the linkage is preferably hydrolysable but stable under conditions of sterilization and storage, and hydrolysable under physiological conditions. Such cationic functional groups (e.g., amino or guanidino groups) may be separated from the backbone by at least one, two, three, four or more atoms.

A tail moiety may be attached to the sterol backbone at $R_{18}$, may have variable chain length or size, and may be charged, uncharged, polar, non-polar, hydrophobic, or amphipathic. The tail moiety may be used to select the hydrophobicity/hydrophilicity of the ceragenin compound. CSA compounds having different degrees of hydrophobicity/hydrophilicity may have different rates of uptake into different target microbes.

The "R" groups described herein, unless specified otherwise, may be substituted or unsubstituted.

With respect to CSA compounds of Formulas I, II, and III (and where not already specified with respect to Formula IV):

each of fused rings A, B, C, and D may be independently saturated, or may be fully or partially unsaturated, provided that at least two of A, B, C, and D is saturated, wherein rings A, B, C, and D form a ring system. Other ring systems can also be used, e.g., 5-member fused rings and/or compounds with backbones having a combination of 5- and 6-membered rings;

$R_1$ through $R_{18}$ are independently selected from the group consisting of hydrogen, hydroxyl, alkyl, hydroxyalkyl, alkyloxyalkyl, alkylcarboxyalkyl, terpenylcarboxyalkyl, terpenylcarbonyloxyalkyl, terpenylamidoalkyl, terpenylaminoalkyl, terpenyloxyoalkyl, alkylaminoalkyl, alkylamino-alkylamino, alkylaminoalkylaminoalkylamino, aminoalkyl, aryl, arylaminoalkyl, haloalkyl, alkenyl, alkynyl, oxo, linking group attached to a second steroid, aminoalkylurethanyl, aminoalkenylurethanyl, aminoalkynylurethanyl, aminoarylurethanyl, aminoalkyloxy, aminoalkylcarboxy, aminoalkyloxyalkyl, aminoalkylaminocarbonyl, aminoalkylcarboxamido, di(alkyl)aminoalkyl, $H_2N-HC(Q_5)-(C=O)-O-$, $H_2N-HC(Q_5)-(C=O)-NH-$, azidoalkyloxy, cyanoalkyloxy, $P.G.-HN-HC(Q_5)-(C=O)-O-$, guanidinoalkyloxy, quaternary ammonium alkylcarboxy, and guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, provided that at least one, and sometimes two, three, or four, of $R_{1-4}$, $R_6$, $R_7$, $R_{11}$, $R_{12}$, $R_{15}$, $R_{16}$, $R_{17}$, and $R_{18}$ are independently selected from the group consisting of aminoalkyl, aminoalkyloxy, aminoalkylcarboxyalkyl, alkylaminoalkyl, alkylamino-alkylamino, alkylamino-alkylaminoalkylamino, aminoalkylcarboxy, arylaminoalkyl, aminoalkyloxyamino, alkylaminocarbonyl, aminoalkylaminocarbonyl, aminoalkyl-carboxyamido, di(alkyl)aminoalkyl, aminoalkylurethanyl, aminoalkenylurethanyl, aminoalkynylurethanyl, aminoarylurethanyl, $H_2N-HC(Q_5)-C(O)-O-$, $H_2N-HC(Q_5)-C(O)-N(H)-$, azidoalkyloxy, cyanoalkyloxy, $P.G.-HN-HC(Q_5)-C(O)-O-$, guanidinoalkyloxy, quaternary ammonium alkylcarboxy, and guanidinoalkylcarboxy.

In embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, substituted or unsubstituted $(C_1-C_{22})$alkyl, substituted or unsubstituted $(C_1-C_{22})$ hydroxyalkyl, substituted or unsubstituted $(C_1-C_{22})$alkyloxy-$(C_1-C_{22})$alkyl, substituted or unsubstituted $(C_1-C_{22})$ alkylcarboxy-$(C_1-C_{22})$alkyl, substituted or unsubstituted $(C_5-C_{25})$terpenylcarboxy-$(C_1-C_{22})$alkyl, substituted or unsubstituted $(C_5-C_{25})$terpenylcarbonyloxy-$(C_1-C_{22})$alkyl, substituted or unsubstituted $(C_5-C_{25})$terpenylcarboxamido-$(C_5-C_{22})$alkyl, substituted or unsubstituted $(C_5-C_{25})$terpenylamino-$(C_5-C_{22})$alkyl, $(C_5-C_{25})$terpenyloxyo-$(C_1-C_{22})$alkyl, substituted or unsubstituted $(C_1-C_{22})$alkylamino-$(C_1-C_{22})$alkyl, substituted or unsubstituted $(C_1-C_{22})$alkylamino-$(C_1-C_{22})$alkylamino, substituted or unsubstituted $(C_1-C_{22})$ alkylamino-$(C_1-C_{22})$alkylamino-$(C_1-C_{22})$alkylamino, substituted or unsubstituted $(C_1-C_{22})$aminoalkyl, substituted or unsubstituted aryl, substituted or unsubstituted arylamino-$(C_1-C_{22})$alkyl, substituted or unsubstituted $(C_1-C_{22})$ haloalkyl, substituted or unsubstituted $(C_2-C_6)$alkenyl, substituted or unsubstituted $(C_2-C_6)$alkynyl, oxo, linking group attached to a second steroid, substituted or unsubstituted $(C_1-C_{22})$aminoalkylurethanyl, substituted or unsubstituted $(C_2-C_{22})$aminoalkenylurethanyl, substituted or unsubstituted $(C_2-C_{22})$aminoalkynylurethanyl, and substituted or unsubstituted aminoarylurethanyl, substituted or unsubstituted $(C_1-C_{22})$aminoalkyloxy, substituted or unsubstituted $(C_1-C_{22})$aminoalkylcarboxy, substituted or unsubstituted $(C_1-C_{22})$aminoalkyloxy-$(C_1-C_{22})$alkyl, substituted or unsubstituted $(C_1-C_{22})$aminoalkyl-aminocarbonyl, substituted or unsubstituted $(C_1-C_{22})$aminoalkylcarboxamido, substituted or unsubstituted di$(C_1-C_{22})$alkylamino-$(C_1-C_{22})$ alkyl, $H_2N-HC(Q_5)-(C=O)-O-$, $H_2N-HC(Q_5)-(C=O)-NH-$, substituted or unsubstituted $(C_1-C_{22})$azidoalkyloxy, substituted or unsubstituted $(C_1-C_{22})$ cyanoalkyloxy, P.G.-HN$-HC(Q_5)-(C=O)-O-$, substituted or unsubstituted $(C_1-C_{22})$guanidinoalkyloxy, substituted or unsubstituted quaternary ammonium $(C_1-C_{22})$ alkylcarboxy, and substituted or unsubstituted $(C_1-C_{22})$guanidinoalkyl carboxy, where $Q_5$ is a side chain of an amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, $(C_1-C_{22})$alkyl, $(C_1-C_{22})$hydroxyalkyl, $(C_1-C_{22})$alkyloxy-$(C_1-C_{22})$alkyl, $(C_1-C_{22})$ aminoalkyl, aryl, $(C_1-C_{22})$haloalkyl, $(C_2-C_6)$alkenyl, $(C_2-C_6)$alkynyl, oxo, a linking group attached to a second steroid, $(C_1-C_{22})$aminoalkyloxy, $(C_1-C_{22})$aminoalkylcarboxy, $(C_1-C_{22})$aminoalkylaminocarbonyl, di$(C_1-C_{22}$ alkyl)amino-$(C_1-C_{22})$alkyl, $H_2N-HC(Q_5)-C(O)-O-$, $H_2N-HC(Q_5)-C(O)-N(H)-$, $(C_1-C_{22})$ azidoalkyloxy, $(C_1-C_{22})$ cyanoalkyloxy, P.G.-HN$-HC(Q_5)-C(O)-O-$, $(C_1-C_{22})$ guanidinoalkyloxy, and $(C_1-C_{22})$ guanidinoalkylcarboxy, where $Q_5$ is a side chain of an amino acid, and P.G. is an amino protecting group;

provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of $(C_1-C_{22})$aminoalkyl, $(C_1-C_{22})$aminoalkyloxy, $(C_1-C_{22})$alkylcarboxy-$(C_1-C_{22})$alkyl, $(C_1-C_{22})$alkylamino-$(C_1-C_{22})$alkylamino, $(C_1-C_{22})$alkylamino-$(C_1-C_{22})$alkylamino-$(C_1-C_{22})$ alkylamino, $(C_1-C_{22})$aminoalkylcarboxy, arylamino-$(C_1-C_{22})$alkyl, $(C_1-C_{22})$aminoalkyloxy $(C_1-C_{22})$ aminoalkylaminocarbonyl, $(C_1-C_{22})$ aminoalkylaminocarbonyl, $(C_1-C_{22})$aminoalkylcarboxyamido, quaternary ammonium $(C_1-C_{22})$ alkylcarboxy, di$(C_1-C_{22}$ alkyl)amino-$(C_1-C_{22})$alkyl, $(C_1-C_{22})$aminoalkylurethanyl, $(C_2-C_{22})$aminoalkenylurethanyl, $(C_2-C_{22})$amino-alkynylurethanyl, aminoarylurethanyl, $H_2N-HC(Q_5)-C(O)-O-$, $H_2N-HC(Q_5)-C(O)-N(H)-$, $(C_1-C_{22})$ azidoalkyloxy, $(C_1-C_{22})$ cyanoalkyloxy, P.G.-HN$-HC(Q_5)-C(O)-O-$, $(C_1-C_{22})$ guanidinoalkyloxy, and $(C_1-C_{22})$ guanidinoalkylcarboxy.

In embodiments, $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted $(C_1-C_6)$ alkyl.

In embodiments, $R_1$, $R_2$, $R_4$, $R_5$, $R_6$, $R_8$, $R_{10}$, $R_{11}$, $R_{14}$, $R_{16}$, and $R_{17}$ are each hydrogen and $R_9$ and $R_{13}$ are each methyl.

In embodiments, $R_3$, $R_7$, $R_{12}$, and $R_{18}$ are independently selected from the group consisting of hydrogen, $(C_1-C_6)$ alkyl, $(C_1-C_6)$hydroxyalkyl, $(C_1-C_{16})$alkyloxy-$(C_1-C_5)$alkyl, $(C_1-C_{16})$alkylcarboxy-$(C_1-C_5)$alkyl, $(C_1-C_{16})$alkylamino-$(C_1-C_5)$alkyl, $(C_1-C_{16})$alkylamino-$(C_1-C_5)$ alkylamino, $(C_1-C_{16})$alkylamino-$(C_1-C_{16})$alkylamino-$(C_1-C_5)$alkylamino, $(C_5-C_{25})$terpenylcarboxy-$(C_1-C_5)$alkyl, $(C_5-C_{25})$terpenylcarbonyloxy-$(C_1C_5)$alkyl, $(C_5-C_{25})$ terpenylcarboxamido-$(C_1-C_5)$alkyl, $(C_5-C_{25})$terpenylamino-$(C_1-C_5)$alkyl, $(C_5-C_{25})$terpenyloxyo-$(C_1-C_5)$alkyl, $(C_1-C_6)$ aminoalkylurethanyl, $(C_2-C_6)$aminoalkenylurethanyl, $(C_2-C_6)$aminoalkynylurethanyl, aminoarylurethanyl, $C_1-C_{16}$ aminoalkyl, arylamino-$(C_1-C_5)$alkyl, $(C_1-C_5)$ aminoalkyloxy, $(C_1-C_{16})$aminoalkyl-oxy-$(C_1-C_5)$alkyl, $(C_1-C_5)$aminoalkylcarboxy, $(C_1-C_5)$aminoalkyl-aminocarbonyl, $(C_1-C_5)$aminoalkylcarboxy-amido, di$(C_1-C_5$ alkyl)amino-$(C_1-C_5)$alkyl, $(C_1-C_5)$guanidinoalkyloxy, quaternary ammonium $(C_1-C_{16})$alkylcarboxy, and unsubstituted $(C_1-C_{16})$ guanidinoalkylcarboxy.

In embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In embodiments, $R_3$, $R_7$, $R_{12}$, and $R_{18}$ are independently selected from the group consisting of aminoalkyloxy, aminoalkylcarboxy, alkylaminoalkyl, alkoxycarbonylalkyl, alkylcarbonylalkyl, di(alkyl)aminoalkyl, alkylcarboxyalkyl, hydroxyalkyl, terpenylcarboxyalkyl, terpenylcarbonyloxyalkyl, terpenylcarboxamido-alkyl, terpenylamino-alkyl, terpenyloxyoalkyl, aminoalkylurethanyl, aminoalkenylurethanyl, aminoalkynyl-urethanyl, and aminoarylurethanyl.

In embodiments, $R_3$, $R_7$, and $R_{12}$ are independently selected from the group consisting of aminoalkyloxy, aminoalkylcarboxy, aminoalkylurethanyl, aminoalkenylurethanyl, aminoalkynylurethanyl, and aminoarylurethanyl.

In embodiments, $R_{18}$ is selected from the group consisting of alkylaminoalkyl, alkoxycarbonylalkyl, alkylcarbonyloxyalkyl, alkylcarbonylalkyl, di(alkyl)aminoalkyl, alkylcarboxyalkyl, hydroxyalkyl, terpenylcarboxyalkyl, terpenylcarbonyloxyalkyl, terpenylcarboxamido-alkyl, terpenylaminoalkyl, and terpenyloxyalkyl.

In embodiments, one or more of rings A, B, C, and D is heterocyclic.

In embodiments, rings A, B, C, and D are non-heterocyclic.

The compounds and compositions disclosed herein are optionally prepared as salts, which advantageously makes them cationic when one or more amine groups is/are protonated. "Salt" as used herein is a broad term, and is to be given its ordinary and customary meaning to a skilled artisan (and is not to be limited to a special or customized meaning), and refers without limitation to a salt of a compound. In embodiments, the salt is an acid addition salt of the compound. Salts can be obtained by reacting a compound with inorganic acids such as hydrohalic acid (e.g., hydrochloric acid or hydrobromic acid), sulfuric acid, nitric acid, phosphoric acid, and phosphonic acid. Salts can also be obtained by reacting a compound with an organic acid such as aliphatic or aromatic carboxylic or sulfonic acids, sulfinic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluenesulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or 1,5-naphthalenedisulfonic acid (NDSA). Salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1-C_7$ alkylamine, cyclohexyl-amine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

In embodiments, the salt is a hydrochloride salt. In embodiments, the salt is a mono-hydrochloride salt, a di-hydrochloride salt, a tri-hydrochloride salt, or a tetra-hydrochloride salt. Additional examples of salts include sulfuric acid addition salts, sulfonic acid addition salts, disulfonic acid addition salts, 1,5-naphthalenedisulfonic acid addition salts, sulfate salts, and bisulfate salts.

"R" groups such as, without limitation, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$, represent substituents that can be attached to the sterol backbone. Unless otherwise specified, an R group may be substituted or unsubstituted.

A "ring" can be heterocyclic or carbocyclic. "Saturated" means a ring in which each atom is either hydrogenated or substituted such that the valency of each atom is filled. "Unsaturated" means a ring where the valency of each atom of the ring may not be filled with hydrogen or other substituents. For example, adjacent carbon atoms in a fused ring can be double bound to each other. Unsaturation can also include deleting at least one of the following pairs and completing the valency of the ring carbon atoms at these deleted positions with a double bond, such as $R_5$ and $R_9$; $R_8$ and $R_{10}$; and $R_{13}$ and $R_{14}$.

Where a group is "substituted" it may be substituted with one, two, three or more of the indicated substituents, which may be the same or different, each replacing a hydrogen atom. If no substituents are indicated, the indicated "substituted" group may be substituted with one or more groups individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, $R_aO(CH_2)_mO—$, $R_b(CH_2)_nO—$, $R_cC(O)O(CH_2)_pO—$, and protected derivatives thereof. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group. A group that is not specifically labeled as substituted or unsubstituted may be considered to be either substituted or unsubstituted.

The terms "$C_a$" or "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having 1 to 4 carbons, that is, $CH_3—$, $CH_3CH_2—$, $CH_3CH_2CH_2—$, $(CH_3)_2CH—$, $CH_3CH_2CH_2CH_2—$, $CH_3CH_2CH(CH_3)—$, $(CH_3)_2CHCH_2—$ and $(CH_3)_3C—$. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

"Alkyl" means a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 15 carbon atoms. The alkyl group could also be a lower alkyl having 1 to 6 carbon atoms. The alkyl group of the compounds may be designated as "$C_4$" or "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, isopropyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

"Alkenyl" means an alkyl group that contains in the straight or branched hydrocarbon chain one or more double bonds. The alkenyl group may have 2 to 25 carbon atoms (whenever it appears herein, a numerical range such as "2 to 25" refers to each integer in the given range; e.g., "2 to 25 carbon atoms" means that the alkenyl group may consist of 2, 3, or 4 carbon atoms, etc., up to and including 25 carbon atoms, although the present definition also covers the occurrence of the term "alkenyl" where no numerical range is designated). The alkenyl group may also be a medium size alkenyl having 2 to 15 carbon atoms. The alkenyl group could also be a lower alkenyl having 1 to 6 carbon atoms. The alkenyl group of the compounds may be designated as "$C_4$" or "$C_2$-$C_4$ alkenyl" or similar designations. An alkenyl group may be unsubstituted or substituted.

"Alkynyl" means an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2, 3, or 4 carbon atoms, etc., up to and including 25 carbon atoms, although the present definition also covers the occurrence of the term "alkynyl" where no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "$C_4$" or "$C_2$-$C_4$ alkynyl" or similar designations. An alkynyl group may be unsubstituted or substituted.

"Aryl" means a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group (although the definition of $C_6$-$C_{10}$ aryl covers the occurrence of "aryl" when no numerical range is designated). Examples of aryl groups include, but are not limited to, benzene, naphthalene and azulene. An aryl group may be substituted or unsubstituted.

"Aralkyl" and "aryl(alkyl)" mean an aryl group connected, as a substituent, via a lower alkylene group. The aralkyl group may have 6 to 20 carbon atoms (whenever it appears herein, a numerical range such as "6 to 20" refers to each integer in the given range; e.g., "6 to 20 carbon atoms" means that the aralkyl group may consist of 6 carbon atom, 7 carbon atoms, 8 carbon atoms, etc., up to and including 20 carbon atoms, although the present definition also covers the occurrence of the term "aralkyl" where no numerical range is designated). The lower alkylene and aryl group of an aralkyl may be substituted or unsubstituted. Examples include but are not limited to benzyl, 2-phenylalkyl, 3-phenylalkyl, and naphthylalkyl.

"Lower alkylene groups" mean a $C_1$-$C_{25}$ straight-chained alkyl tethering groups, such as —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

"Cycloalkyl" means a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

"Cycloalkenyl" means a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

"Cycloalkynyl" means a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

"Alkoxy" or "alkyloxy" mean the formula —OR wherein R is an alkyl, an alkenyl, an alkynyl, a cycloalkyl, a cycloalkenyl or a cycloalkynyl as defined above. Examples of alkoxys are methoxy, ethoxy, n-propoxy, 1-methylethoxy (isopropoxy), n-butoxy, iso-butoxy, sec-butoxy and tert-butoxy. An alkoxy may be substituted or unsubstituted.

"Acyl" means a hydrogen, alkyl, alkenyl, alkynyl, aryl, or heteroaryl connected, as substituents, via a carbonyl group, such as —(C=O)—R. Examples include formyl, acetyl, propanoyl, benzoyl, and acryl. An acyl may be substituted or unsubstituted.

"Alkoxyalkyl" or "alkyloxyalkyl" mean an alkoxy group connected, as a substituent, via a lower alkylene group. Examples include alkyl-O-alkyl- and alkoxy-alkyl- with the terms alkyl and alkoxy defined herein.

"Hydroxyalkyl" means an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

"Haloalkyl" means an alkyl group in which one or more of the hydrogen atoms are replaced by a halogen (e.g., mono-haloalkyl, di-haloalkyl and tri-haloalkyl). Examples include chloromethyl, fluoromethyl, difluoromethyl, trifluoromethyl and 1-chloro-2-fluoromethyl, 2-fluoroisobutyl. A haloalkyl may be substituted or unsubstituted.

"Amino" means "—$NH_2$".

"Hydroxy" means "—OH".

"Cyano" means "—CN".

"Carbonyl" or "oxo" mean "—C=O".

"Azido" means "—N".

"Aminoalkyl" means an amino group connected, as a substituent, via a lower alkylene group. Examples include $H_2N$-alkyl- with the term alkyl defined herein.

"Alkylcarboxyalkyl" means an alkyl group connected, as a substituent, to a carboxy group that is connected, as a substituent, to an alkyl group. Examples include alkyl-(C=O)—O-alkyl- and alkyl-O—(C=O)-alkyl- with the term alkyl as defined herein.

"Alkylaminoalkyl" means an alkyl group connected, as a substituent, to an amino group that is connected, as a substituent, to an alkyl group. Examples include alkyl-NH-alkyl- with the term alkyl as defined herein.

"Dialkylaminoalkyl" and "di(alkyl)aminoalkyl" mean two alkyl groups connected, each as a substituent, to an amino group that is connected, as a substituent, to an alkyl group. Examples include

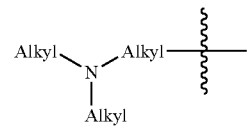

with the term alkyl as defined herein.

"Alkylaminoalkylamino" means an alkyl group connected, as a substituent, to an amino group that is connected, as a substituent, to an alkyl group that is connected, as a substituent, to an amino group. Examples include alkyl-NH-alkyl-NH— with the term alkyl as defined herein.

"Alkylaminoalkylaminoalkylamino" means an alkyl group connected, as a substituent, to an amino group that is connected, as a substituent, to an alkyl group that is connected, as a substituent, to an amino group that is connected, as a substituent, to an alkyl group. Examples include alkyl-NH-alkyl-NH-alkyl- with the term alkyl as defined herein.

"Arylaminoalkyl" means an aryl group connected, as a substituent, to an amino group that is connected, as a substituent, to an alkyl group. Examples include aryl-NH-alkyl- with the terms aryl and alkyl as defined herein.

"Aminoalkyloxy" means an amino group connected, as a substituent, to an alkyloxy group. Examples include $H_2N$-alkyl-O— and $H_2N$-alkoxy- with the terms alkyl and alkoxy as defined herein.

"Aminoalkyloxyalkyl" means an amino group connected, as a substituent, to an alkyloxy group connected, as a substituent, to an alkyl group. Examples include $H_2N$-alkyl-O-alkyl- and $H_2N$-alkoxy-alkyl- with the terms alkyl and alkoxy as defined herein.

"Aminoalkylcarboxy" means an amino group connected, as a substituent, to an alkyl group connected, as a substituent, to a carboxy group. Examples include H$_2$N-alkyl-(C=O)—O— and H$_2$N-alkyl-O—(C=O)— with the term alkyl as defined herein.

"Aminoalkylaminocarbonyl" means an amino group connected, as a substituent, to an alkyl group connected, as a substituent, to an amino group connected, as a substituent, to a carbonyl group. Examples include H$_2$N-alkyl-NH—(C=O)— with the term alkyl as defined herein.

"Aminoalkylcarboxamido" means an amino group connected, as a substituent, to an alkyl group connected, as a substituent, to a carbonyl group connected, as a substituent to an amino group. Examples include H$_2$N-alkyl-(C=O)—NH— and H$_2$N-alkyl-NH—(C=O)— with the term alkyl as defined herein.

"Azidoalkyloxy" means an azido group connected as a substituent, to an alkyloxy group. Examples include N$_3$-alkyl-O— and N$_3$-alkoxy- with the terms alkyl and alkoxy as defined herein.

"Cyanoalkyloxy" means a cyano group connected as a substituent, to an alkyloxy group. Examples include NC-alkyl-O— and NC-alkoxy- with the terms alkyl and alkoxy as defined herein.

"Sulfenyl" means "—SR" in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A sulfenyl may be substituted or unsubstituted.

"Sulfinyl" means "—(S=O)—R" in which R can be the same as defined with respect to sulfenyl. A sulfinyl may be substituted or unsubstituted.

"Sulfonyl" means "—(S=O)—OR" in which R can be the same as defined with respect to sulfenyl. A sulfonyl may be substituted or unsubstituted.

"O-carboxy" means "R—(C=O)—O—" in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted or unsubstituted.

"Ester" and "C-carboxy" mean "—(C=O)—OR" in which R can be the same as defined with respect to O-carboxy. An ester and C-carboxy may be substituted or unsubstituted.

"Thiocarbonyl" means "—(C=S)—R" in which R can be the same as defined with respect to O-carboxy. A thiocarbonyl may be substituted or unsubstituted.

"Trihalomethanesulfonyl" means "X$_3$CSO$_2$—" wherein X is a halogen.

"S-sulfonamido" means "—SO$_2$N(RARB)" in which RA and RB can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An S-sulfonamido may be substituted or unsubstituted.

"N-sulfonamido" means "RSO$_2$N(RA)-" in which R and RA can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-sulfonamido may be substituted or unsubstituted.

"O-carbamyl" and "urethanyl" mean "—O—(C=O)—N(RARB)" in which RA and RB can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-carbamyl or urethanyl may be substituted or unsubstituted.

"N-carbamyl" means "RO—(C=O)—N(RA)-" in which R and RA can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-carbamyl may be substituted or unsubstituted.

"O-thiocarbamyl" means "—O—(C=S)—N(RARB)" in which RA and RB can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-thiocarbamyl may be substituted or unsubstituted.

"N-thiocarbamyl" means "RO—(C=S)—N(RA)-" in which R and RA can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-thiocarbamyl may be substituted or unsubstituted.

"C-amido" means "—(C=O)—N(RARB)" in which RA and RB are independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A C-amido may be substituted or unsubstituted.

"N-amido" means "R—(C=O)—N(RA)-" in which R and RA are independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-amido may be substituted or unsubstituted.

"Guanidinoalkyloxy" means a guanidinyl group connected, as a substituent, to an alkyloxy group. Examples are

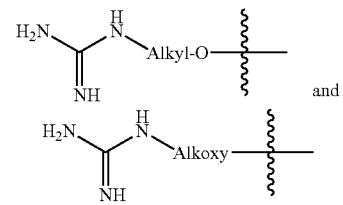

with the terms alkyl and alkoxy as defined herein.

"Guanidinoalkylcarboxy" means a guanidinyl group connected, as a substituent, to an alkyl group connected, as a substituent, to a carboxy group. Examples are

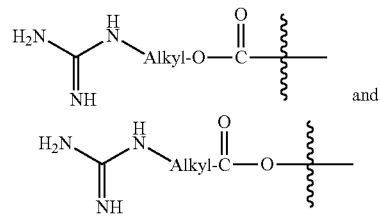

with the term alkyl as defined herein.

"Quaternary ammonium alkylcarboxy" means a quaternized amino group connected, as a substituent, to an alkyl group connected, as a substituent, to a carboxy group. Examples are with

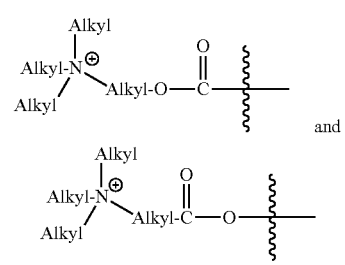

the term alkyl as defined herein.

"Halogen atom" and "halogen" mean any one of the radio-stable atoms of column 7 of the Periodic Table of the Elements, such as, fluorine, chlorine, bromine and iodine.

Where the number of substituents is not specified (e.g. haloalkyl), there may be one or more substituents present. For example, "haloalkyl" may include one or more of the same or different halogens.

"Amino acid" means any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, γ-aminobutyric acid, citrulline, β-alanine, α-ethylglycine, α-propyl-glycine and norleucine.

A "linking group" is a divalent moiety used to link one steroid to another steroid. In embodiments, the linking group is used to link a first CSA with a second CSA (which may be the same or different). An example of a linking group is $(C_1-C_{10})$alkyloxy-$(C_1-C_{10})$alkyl.

"P.G." or "protecting group" or "protecting groups" mean any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4''-trimethoxytrityl (TMTr); and those described herein). Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of treating a coronavirus infection in a subject, the method comprising:
providing a deactivation composition including a cationic steroidal antimicrobial (CSA) compound in a carrier, wherein the CSA compound has a chemical structure of Formula IV, or salt thereof:

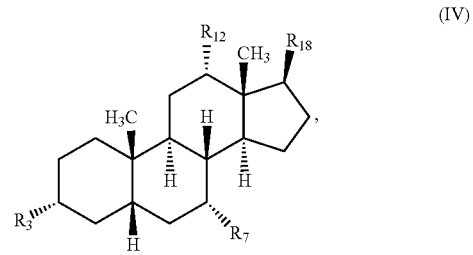

where,
$R_3$, $R_7$, and $R_{12}$ are independently selected from the group consisting of aminoalkyloxy, aminoalkylcarboxy, aminoalkylurethanyl, aminoalkenyl-urethanyl, aminoalkynylurethanyl, and aminoarylurethanyl; and
$R_{18}$ is selected from the group consisting of alkylaminoalkyl, alkoxycarbonylalkyl, alkylcarbonyloxyalkyl, alkylcarbonylalkyl, di(alkyl)aminoalkyl, alkylcarboxyalkyl, hydroxyalkyl, terpenylcarboxyalkyl, terpenylcarbonyloxyalkyl, terpenylcarboxamido-alkyl, terpenylaminoalkyl, and terpenyloxyoalkyl; and administering the deactivation composition to the subject, wherein the deactivation composition treats the coronavirus infection in the subject by deactivating coronavirus virions in the subject or that come into contact with the subject.

2. The method of claim 1, wherein the subject is a human, livestock animal, poultry, pet, laboratory animal, or zoo animal.

3. The method of claim 1, wherein deactivation composition is administered topically.

4. The method of claim 1, wherein the deactivation composition is provided in the form of a liniment, salve, lotion, ointment, cream, powder, soap, wash, or spray.

5. The method of claim 1, wherein the deactivation composition is administered via inhalation.

6. The method of claim 5, wherein the deactivation composition is provided as an aqueous solution capable of being nebulized.

7. The method of claim 5, wherein the deactivation composition is administered using a metered-dose inhaler, a nebulizer, and/or a dry powder dispersion device.

8. The method of claim 5, wherein the carrier comprises one or more of saline solution, bulking powders, carbohydrates, disaccharides, oligo- or polysaccharides, alcohols or polyalcohols, salts, amino acids, buffers, or combinations thereof.

9. The method of claim 1, wherein the deactivation composition is administered orally or parenterally.

10. The method of claim 1, wherein the carrier comprises one or more of water, alcohol, other organic solvents, an emulsion, or combinations thereof.

11. The method of claim 1, wherein the CSA compound is selected from the group consisting of CSA-13, CSA-27, CSA-28, CSA-30, CSA-31, CSA-32, CSA-33, CSA-34, CSA-35, CSA-36, CSA-37, CSA-41, CSA-42, CSA-43, CSA-44, CSA-45, CSA-47, CSA-49, CSA-50, CSA-51, CSA-52, CSA-56, CSA-61, CSA-90, CSA-131, CSA-136, CSA-137, CSA-138, CSA-141, CSA-142, CSA-144, CSA-145, CSA-146, CSA-148, CSA-190, CSA-191, CSA-192, CSA-255, CSA-256, and CSA-257.

12. A method of treating a coronavirus infection in a subject, the method comprising:
providing a deactivation composition including one or more cationic steroidal antimicrobial (CSA) compounds in a carrier, the one or more CSA compounds having a chemical structure of Formula IV, or salt thereof:

(IV)

where,
$R_3$, $R_7$, and $R_{12}$ are independently selected from the group consisting of aminoalkyloxy and aminoalkylcarboxy; and
$R_{18}$ is selected from the group consisting of alkylaminoalkyl, di(alkyl)aminoalkyl, and alkylcarboxyalkyl; and
administering the deactivation composition to the subject, wherein the deactivation composition treats the coronavirus infection in the subject by deactivating coronavirus virions in the subject or that come into contact with the subject.

13. The method of claim 12, wherein the subject is a human, livestock animal, poultry, pet, laboratory animal, or zoo animal.

14. The method of claim 12, wherein the carrier comprises one or more of saline solution, bulking powders, carbohydrates, disaccharides, oligo- or polysaccharides, alcohols or polyalcohols, salts, amino acids, buffers, or combinations thereof and the deactivation composition is administered via inhalation.

15. The method of claim 12, wherein the deactivation composition is provided as an aqueous solution capable of being nebulized.

16. The method of claim 15, wherein the deactivation composition is administered using a metered-dose inhaler, a nebulizer, and/or a dry powder dispersion device.

17. The method of claim 12, wherein the carrier comprises one or more of water, alcohol, other organic solvents, an emulsion, or combinations thereof.

18. The method of claim 12, wherein the CSA compound is selected from the group consisting of CSA-13, CSA-18, CSA-22, CSA-38, CSA-43, CSA-44, CSA-45, CSA-46, CSA-53, CSA-90, CSA-91, CSA-92, CSA-93, CSA-93, CSA-97, CSA-98, CSA-99, CSA-103, CSA-130, CSA-131, CSA-132, CSA-133, CSA-134, CSA-135, CSA-136, CSA-137, CSA-138, CSA-141, CSA-142, CSA-144, CSA-145, CSA-146, CSA-148, CSA-190, CSA-191, CSA-192, CSA-192MS, CSA-255, CSA-256, CSA-257, and CSA-258.

19. A method of treating a coronavirus infection in a subject, the method comprising:
providing a deactivation composition including one or more cationic steroidal antimicrobial (CSA) compounds in a carrier, wherein the one or more CSA compounds are selected from the group consisting of: CSA-13, CSA-43, CSA-44, CSA-45, CSA-90, CSA-131, CSA-136, CSA-137, CSA-138, CSA-141, CSA-142, CSA-144, CSA-145, CSA-146, and CSA-148; and
administering the deactivation composition to the subject, wherein the deactivation composition treats the coronavirus infection in the subject by deactivating coronavirus virions in the subject or that come into contact with the subject.

20. The method of claim 19, wherein the carrier comprises one or more of saline solution, bulking powders, carbohydrates, disaccharides, oligo- or polysaccharides, alcohols or polyalcohols, salts, amino acids, buffers, or combinations thereof and the deactivation composition is administered via inhalation.

* * * * *